US010929935B1

(12) United States Patent
Frankenfield et al.

(10) Patent No.: US 10,929,935 B1
(45) Date of Patent: Feb. 23, 2021

(54) RETAIL HSA FUNDING AND PAYMENT MECHANISM

(71) Applicant: ConnectYourCare, LLC, Hunt Valley, MD (US)

(72) Inventors: Jennifer Frankenfield, Old Hickory, TN (US); Vrajesh Bhavsar, Franklin, TN (US)

(73) Assignee: ConnectYourCare, LLC, Hunt Valley, MD (US)

( * ) Notice: Subject to any disclaimer, the term of this patent is extended or adjusted under 35 U.S.C. 154(b) by 0 days.

(21) Appl. No.: 16/731,223

(22) Filed: Dec. 31, 2019

(51) Int. Cl.
*G06Q 40/00* (2012.01)
*G06Q 20/20* (2012.01)
*G06Q 20/40* (2012.01)
*G06Q 20/22* (2012.01)
*G06Q 40/08* (2012.01)

(52) U.S. Cl.
CPC ........... *G06Q 40/10* (2013.01); *G06Q 20/206* (2013.01); *G06Q 20/223* (2013.01); *G06Q 20/4014* (2013.01); *G06Q 20/4037* (2013.01); *G06Q 40/08* (2013.01)

(58) Field of Classification Search
CPC ...... G06Q 40/00; G06Q 40/10; G06Q 20/206; G06Q 20/223; G06Q 220/4014; G06Q 20/4037; G06Q 40/08
See application file for complete search history.

(56) References Cited

U.S. PATENT DOCUMENTS

| | | | | |
|---|---|---|---|---|
| 9,390,417 | B2 * | 7/2016 | Song ................... | G06Q 40/12 |
| 2007/0185803 | A1 * | 8/2007 | Harrison .............. | G06Q 40/10 705/36 T |
| 2009/0216672 | A1 * | 8/2009 | Zulf ..................... | G06Q 40/00 705/35 |
| 2011/0145007 | A1 * | 6/2011 | Romanini ............ | G06Q 50/22 705/2 |

(Continued)

OTHER PUBLICATIONS

Insurer's Bank, Exante, Exploits an Edge in HSAs Garmhausen, Steve. American Banker; New York, N.Y. [New York, N.Y]May 31, 2006: 5. (Year: 2006).*

*Primary Examiner* — Lalita M Hamilton
(74) *Attorney, Agent, or Firm* — Sterne, Kessler, Goldstein & Fox P.L.L.C.

(57) ABSTRACT

Disclosed herein are system, method, and computer program product embodiments describing the creation and funding of tax-advantaged accounts at a point of sale. By immediately funding the tax-advantaged account at the point of sale using a funding and payment mechanism, the disclosed embodiments may effectively and instantly fund a tax-advantaged account at a point of sale. The funding and payment mechanism overcomes the lapse in availability of funds inherent in legacy systems. Thus, an account holder may then immediately pay a provider from the tax-advantaged account for qualified expenses. The disclosure also presents a credit feature allow prospective account holders to initially fund the tax-advantaged account. At the point of sale, the prospective account holder may link their newly created tax- (Continued)

advantaged account to other accounts, allowing the system to detect potential over-contributions. The disclosure also presents a retroactive analysis feature that analyzes linked accounts to create tax-advantaged transactions in transactions completed earlier in a plan year.

20 Claims, 10 Drawing Sheets

(56) References Cited

U.S. PATENT DOCUMENTS

| | | | |
|---|---|---|---|
| 2013/0124286 A1* | 5/2013 | Chen | G06Q 20/405 705/14.23 |
| 2016/0012465 A1* | 1/2016 | Sharp | G06Q 20/10 705/14.17 |
| 2018/0268109 A1* | 9/2018 | Ramgir | A61B 5/0022 |

* cited by examiner

RETAIL HSA FUNDING AND PAYMENT MECHANISM

BACKGROUND

A tax-advantaged account (TAA) provides tax advantages to account holders. An account holder may deposit funds pre-tax into the TAA, earn tax-free interest on those deposits, and withdraw funds tax-free for qualified expenses. A qualified expense is an expenditure incurred during a plan year that satisfies eligibility restrictions, which may vary by account type. Account holders may create a TAA through an employer or in their individual capacity. An account holder may contribute to a TAA at any time during a tax year, but regulations may cap the amount that an account holder may contribute in a plan year based on the account type. A plan manager or administrator may create, administer, and manage TAAs on behalf of account holders and provide tools and ancillary services related to the TAAs.

An individual may employ a TAA to cover qualified expenses. Eligibility restrictions establish expenditures that are qualified expenses in a TAA. For example, a qualified medical expense may be a medical, dental, or other suitable expense that qualifies for an itemized deduction on an account holder's taxes. A qualified medical expense may include the cost of diagnosis, cure, mitigation, treatment, or prevention of disease, such as payment for legal medical services rendered by physicians, pharmacists, dentists, and other medical practitioners and the related costs of equipment, supplies, therapeutics, and diagnostic devices. An account holder, an account holder's spouse, or any dependents claimed by the account holder on a tax return may incur a qualified medical expense. Eligibility restrictions may vary based on the account type.

To create a qualified expense, a TAA must exist before the account holder pays for the expense. Legacy systems do not have the infrastructure needed to complete the steps of creating the account, funding the account, and rendering payment from the created account at a point of sale. Instead, legacy systems require a clearing house or settlement facility to fund a TAA with an initial contribution amount. Transactions conducted using an ACH transaction may take several hours or days to complete. This delay is unacceptable to retailers at a point of sale, and legacy systems fail to offer the ability to create and immediately fund a TAA. A prospective account holder without a TAA who is rendering payment to a provider at a point of sale may thus miss significant tax savings for expenses that could be qualified expenses if the individual possessed a TAA.

Accordingly, a need exists to create and fund a TAA at a point of sale so that a prospective account holder may immediately pay for a qualified expense from the TAA. This process of creating and funding an account and immediately rendering payment to the provider may be referred to throughout the below disclosure as the Retail HSA process. The leveraging of the contribution payment mechanism within the Retail HSA process provides a further technical improvement of enhancing security in the provider-payment process because the required transactions finalize in real-time or near real-time. Another technical improvement is realized by eliminating excess storage needed to preserve and maintain transactions that would other take hours or days to finalize and clear.

Legacy systems also fail to properly detect over-contributions across multiple TAAs. Such an over-contribution, i.e., an excess contribution, may result in tax penalties being assessed against an account holder. For example, regulations may limit HSA contributions in a year to $7,000 for a household, and if two members of the household each separately open an HSA and fund the HSA with $7,000, the total contribution for the household would amount to $14,000. This would exceed the contribution limit, and the household may face tax penalties on the excess contribution. Such over-contribution management is especially relevant when opening and funding an HSA at a point of sale, when large contributions often occur to cover large expenses.

Accordingly, a need exists to perform automated over-contribution analysis at a point of sale when initially creating and funding a TAA. By linking TAAs in this fashion, the Retail HSA system may detect over-contributions across multiple TAAs considering a specified initial funding amount. The Retail HSA system may alert the prospective account holder of the potential over-contribution and provide procedural options to remedy the defect. This provides a further technical benefit in ensuring that database tables storing TAA-account information do not include dangling references or other corrupted data when contributions roll back in response to over-contributions. Furthermore, it obviates the need for an administrator to manually update the tables to cure an over-contribution scenario.

Legacy systems also fail to accommodate prospective account holders who lack sufficient initial funding, e.g., an individual who cannot initially fund a TAA to the extent necessary to cover the cost of a provided system and create a qualified expense. Such an individual may generally open an external line of credit, i.e., not a TAA, to render payment for the qualified expense. In such a circumstance, the individual may miss out on any tax-savings related to a qualified expense.

Accordingly, a need exists to provide a credit feature within the Retail HSA process. By leveraging this feature, an account holder may simultaneously receive crediting options and agree to the loan terms while creating and funding a TAA. The line of credit may then be used to immediately fund the newly created TAA and render payment to the provider from the TAA. The transaction may create a qualified expense for the account holder, where otherwise the rendering of payment via the line of credit would not qualify for any tax benefits.

Legacy systems also fail to provide account holders with the ability to create qualified expenses from past expenditures, i.e., expenses that the account holder paid for previously in a plan year. For instance, a prospective account holder may have paid for a number of expenses from a checking or banking account in the months prior to creating a TAA. The account holder may thus fail to create qualified expenses and realize tax savings for these expenditures.

Accordingly, a need exists to perform retroactive analysis against expenditures in a linked account to determine qualified expenses that occurred in a plan year. A management system may perform retroactive analysis during the creation and funding of a TAA. The Retail HSA system may identify eligible transactions in the linked accounts and create qualified expenses in the newly created TAA representing the eligible transactions that occurred previously in the plan year. In other embodiments, retroactive analysis may occur when an account holder creates an account through a management interface or at an account holder's request against an already existing account.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Figure 1:
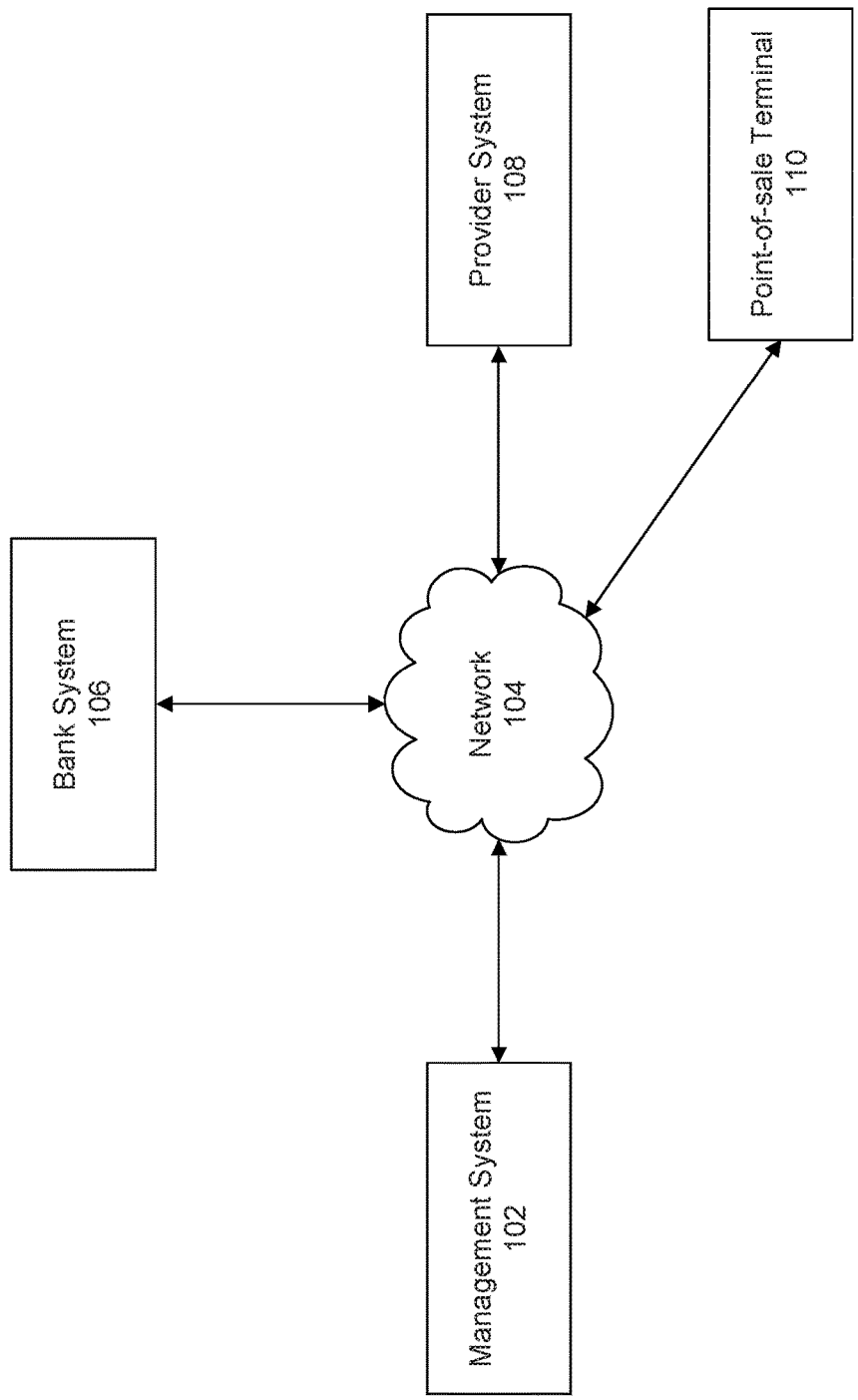
FIG. 1 is an example block diagram illustrating multiple systems involved in creating and funding a TAA at a point of sale and managing the TAA after creation, according to an example embodiment.

Provided herein are system, apparatus, device, method and/or computer program product embodiments, and/or combinations and sub-combinations thereof, for creating and funding TAAs at a point of sale using a Retail HSA funding and payment mechanism. Further embodiments offer account holders a credit feature to initially fund a TAA and link a newly created TAA to external accounts, including bank accounts and other TAAs, to allow a plan management system to perform over-contribution analysis. The disclosure also presents a retroactive analysis feature that analyzes linked accounts and creates a qualified expense for expenditures incurred earlier in a plan year, allowing an account holder to realize additional tax benefits.

A TAA is an account offering tax benefits or tax exemptions. Examples of TAAs include: health savings accounts (HSA), health reimbursement arrangements (HRA), flexible spending accounts (FSA), individual retirement accounts (IRA), and other types of contribution funded accounts (CFA). TAAs may provide investment options that allow deposited funds to accrue interest over time and leverage investment vehicles such as bonds, stocks, mutual funds, annuities, money market accounts, bank accounts, or other suitable assets.

Depending on the TAA type, the TAA may be employer funded, employee funded, or both employer and employee funded. An employer-sponsored plan may allow the individual to contribute a portion of their pre-tax earnings at the end of each pay period to fund the TAA. An account holder may also open and fund a TAA in their individual capacity. The individual may make ad-hoc contributions to a TAA. For example, an individual may establish an HSA through a qualified HSA trustee. An individual opening a TAA may also need to meet certain eligibility criteria, e.g., for an HSA, an individual may need to possess a high deductible health plan, have no other disqualifying healthcare coverage, not be enrolled in Medicare, and not be named as a dependent on someone else's tax return.

A plan manager or plan administrator may manage TAAs on behalf of account holders. The plan manager may incorporate the TAA into a management system including multiple TAAs (e.g., CFAs, HSAs, HRAs, FSAs, IRAs, etc.), bank accounts, credit cards, benefit plans, auto-deposit configurations, withdrawal mechanisms, etc. The management system may manage investments in the TAAs, furnish an identification card and/or debit card, offer financial services, and provide other ancillary services and features.

The management system may provide accelerated access to funds within a TAA, such as an HSA, through a corresponding contribution funded on-demand account. By enabling an employee accelerated access to future contributions stored within the on-demand account, an employee may more likely be able to pay for larger qualified expenses from the first day of the plan year. Greater detail for providing an on-demand based account is provided in reference to U.S. Non-Provisional application Ser. No. 15/651,645, which issued as U.S. Pat. No. 10,032,217, which is incorporated by reference herein in its entirety.

An account holder may link a TAA with a payment card, e.g., a debit card, or any electronic or other funding mechanism enabling the individual to access funds within the TAA to pay for qualified expenses. The individual may further establish a hierarchical payment methodology in a management system, by providing multiple accounts with associated priorities to pay for qualified expenses. Greater detail for providing flexible and prioritized multi-purse tables is provided in reference to U.S. Non-Provisional application Ser. No. 15/282,244, which is hereby incorporated by reference herein in its entirety.

The management system may automatically adjudicate real-time card transactions. Greater detail for auto-adjudicating real-time card transactions using delayed transaction records is provided in reference to U.S. Non-Provisional application Ser. No. 15/239,691, which is hereby incorporated by reference herein in its entirety.

The management system may allow the configuration of an asset transfer on demand account that eliminates blackout periods. Such blackout periods may occur when TAA funds move from one bank to another in response to a provider change or job change. Greater detail on the asset transfer on demand system is provided in U.S. Non-Provisional application Ser. No. 15/887,757, which is hereby incorporated by reference herein in its entirety.

A management system may verify a prospective account holder's identity and create and fund a TAA a point of sale. Greater detail for the identity verification system is provided in reference to U.S. Non-Provisional application Ser. No. 15/958,937, which is hereby incorporated by reference herein in its entirety.

FIG. 1 illustrates system 100 that creates and funds a TAA at a point of sale and manages the TAA after creation, according to an example embodiment. System 100 includes management system 102, bank system 106, provider system 108, and point-of-sale terminal 110, connected via network 104. Each of the systems or components may be implemented using one or more processors. Although FIG. 1 depicts the subsystems as remote systems connected via network 104, one or more systems may be operated by or maintained by one entity. For example, provider system 108 and point-of-sale terminal 110 may co-exist as part of a single system operated by one entity.

Management system 102 may manage, create, and maintain TAAs and provide related services and functions. Management system 102 may store user-identifying information, employment information, and other related information. Management system 102 may link multiple TAAs, bank accounts, credit cards, and benefit plans for an account holder. Management system 102 may provide auto-deposits, withdrawal mechanisms, tools to manage investments, ancillary management tools, etc. Management system 102 may leverage on-demand accounts, multi-purse technologies, and real-time auto-adjudication of claims. Management system 102 may determine whether expenses qualify as qualified expenses. Management system 102 may coordinate new account creation for account holders and prospective account holders in the Retail HSA setting, as described in further detail below, and also through a web interface, via employer configurations, and other suitable use cases. Management system 102 may create and fund a new TAA at a point of sale and render immediate payment to a provider from the TAA, offer crediting options during the Retail HSA process, and perform over-contribution analysis and retroactive analysis.

Network 104 may enable management system 102 to communicate with bank system 106, provider system 108, and point-of-sale terminal 110. Network 104 may be an enterprise wide area network (WAN) employing Ethernet communications, a LAN, the Internet, or other public or private network, although network 104 may employ other wired and/or wireless communication techniques, protocols, and technologies.

Bank system 106 may be employed by a bank or other qualified institution to store information about account holders and their bank accounts. Bank system 106 may further accept deposits, process withdrawals, render payment for purchases, etc. In an embodiment, bank system 106 may receive and send web service requests via network 104 to transfer funds and create accounts. Bank system 106 may expose various web services and respond to suitably formed API calls to transact among bank accounts.

Provider system 108 may allow a provider to manage account information, generate bills, receive payments, etc. at locations that provide qualified goods and services. For example, providers of qualified medical services may be physicians, surgeons, dentists, and other suitable medical practitioners. Provider system 108 may track information about customers, patients, or individuals. Provider system 108 may generate bills for any services provided or associated expenses accrued and initiate banking transactions to receive payment for services rendered from TAAs, credit card accounts, debit accounts, etc. Provider system 108 may accept cash payment for services rendered. Provider system 108 may interact with management system 102 to create and fund TAAs as described in further detail below.

Point-of-sale terminal 110 may be a card-swiping machine, laptop computer, desktop computer, mobile device, or other suitable computing device that interacts with the various subsystems in system 100, including management system 102, network 104, bank system 106, and provider system 108, at the point of sale to create and fund a TAA and transact from the newly created TAA. Point-of-sale terminal 110 may view information stored on any of the depicted systems in the form of HTML pages or other suitable web transmissions. In an alternate embodiment, point-of-sale terminal 110 may be communicatively coupled or contained in the same physical machine as provider system 108. Point-of-sale terminal 110 may provide prospective account holders with the ability to link accounts, perform over-contribution analysis, harness credit features, perform retroactive analysis of linked accounts, and otherwise engage in the Retail HSA process.

Figure 2:
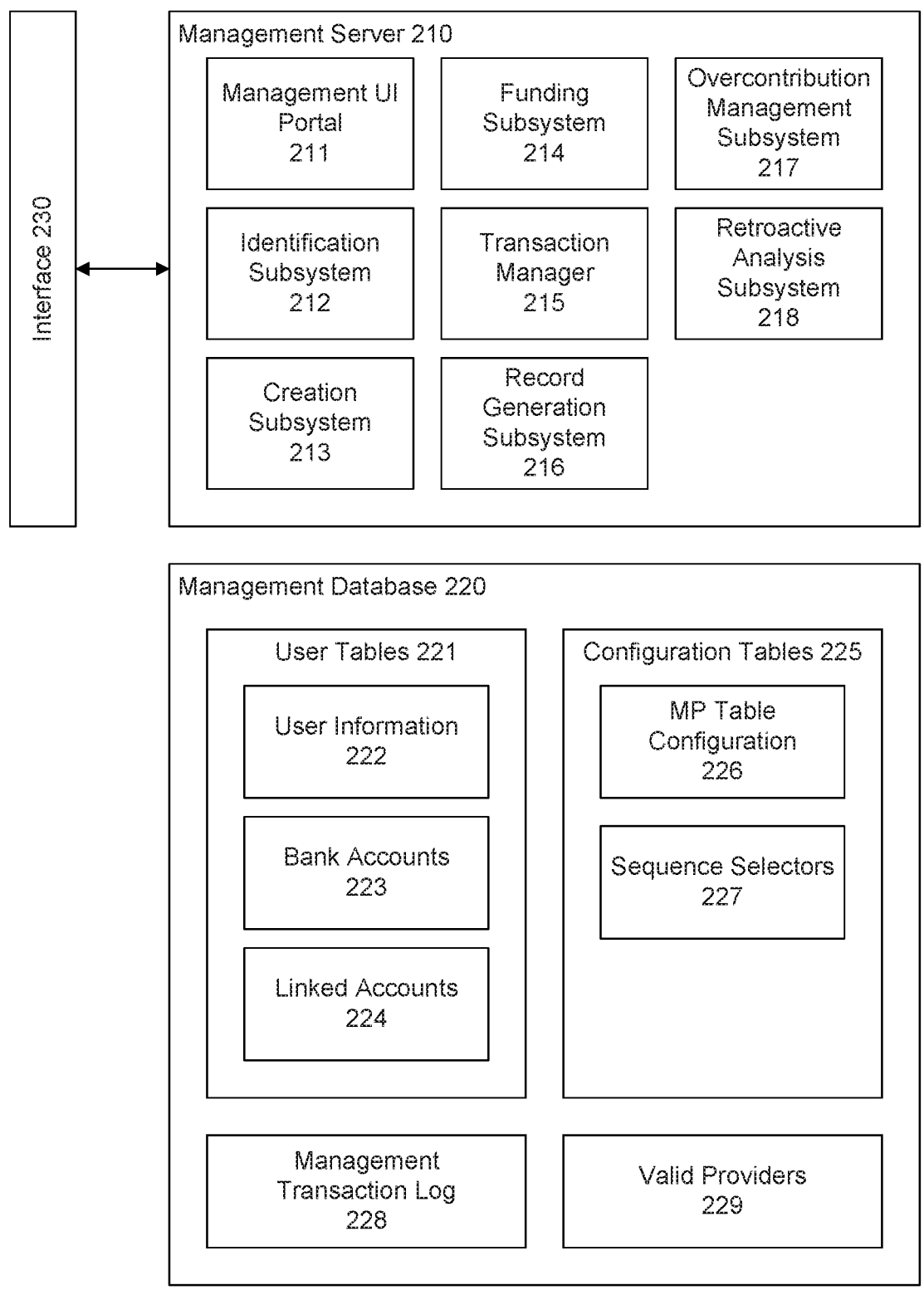
FIG. 2 is an example block diagram illustrating a management system, according to an example embodiment.

FIG. 2 illustrates management system 200 that creates, maintains, configures, and manages TAAs, bank accounts, benefit plans, etc. of individuals, organizations, or other suitable entities, according to an example embodiment. Management system 200 may be an embodiment of management system 102 of FIG. 1. Management system 200 may include management server 210, management database 220, and interface 230. Though depicted as a single server, management server 210 may in some embodiments be representative of a plurality of servers, each of which may be implemented by one or more processors. Likewise, management database 220 may represent a plurality of databases coupled to a plurality of management servers. Management database 220 may be implemented on one or more storage devices.

Management server 210 may include management UI portal 211, identification subsystem 212, creation subsystem 213, funding subsystem 214, transaction manager 215, record generation subsystem 216, funding subsystem 214, over-contribution subsystem 217, and retroactive analysis subsystem 218. One or more of the depicted components may be implemented as processing systems comprising one or more sub-components. These sub-components may include an interface for communicating within and/or across systems and a distribution component for sending information to other components and/or across systems.

Management UI portal 211 may allow an individual to create accounts, maintain benefit plan offerings, and view/adjust other related information and settings. Management UI portal 211 may allow the individual to view TAA details or benefit plan details including statuses, balances, and transactions. Management UI portal 211 may verify the identity of the individual or plan manager using an encrypted login/password combination or appropriate identification methodology. Management UI portal 211 may allow an individual to generate records of qualified expenses for the purposes of tax-advantage recordkeeping. Adjustments made within management UI portal 211 may propagate to bank system 106 and/or provider system 108. Management UI portal 211 may provide analytics and report generation capabilities. Management UI portal 211 may also accommodate transmissions from point-of-sale terminal 110 to create and fund a new TAA for a prospective account holder. In an embodiment, management UI portal 211 may provide to a prospective account holder user interfaces allowing the account holder to link externally held TAAs and perform over-contribution analysis and retroactive analysis against linked TAAs. In another embodiment, management UI portal 211 may provide a user interface that allows an account holder to select lending options and leverage crediting features provided by the Retail HSA system.

Identification subsystem 212 may verify the identity of a prospective account holder opening a TAA at a point of sale. Identification subsystem 212 may receive an identity verification request from provider system 108 or point-of-sale terminal 110. Identification subsystem 212 may receive uniquely identifying information from provider system 108 or point-of-sale terminal 110 including a full name, social security number, or other suitable information about the prospective account holder. In one embodiment, identification subsystem 212 may send a web transmission, e.g., a web service request, to a qualified identity verification agent and receive in response an identity verification. In an alternate embodiment, a representative of the provider at the point of sale may verify the identity of the prospective account holder by checking a driver's license or other suitable identification. In this embodiment, identification subsystem 212 may receive with the verification request a confirmation that the prospective account holder provided necessary documentation.

Creation subsystem 213 may create account information for the prospective account holder in management database 220 and across the subsystems in system 100. Creation subsystem 213 may use identifying information, e.g., full name, social security number, etc., to uniquely identify the prospective account holder. Creation subsystem 213 may also create an identification number specific to management system 102 and use the unique identifier throughout tables in management database 220 to identify the prospective account holder. Creation subsystem 213 may receive additional information about the prospective account holder including: credit card accounts, debit accounts, other funding sources, etc., for prioritizing into a hierarchical account structure at the time of account creation.

Funding subsystem 214 may receive from point-of-sale terminal 110 or provider system 108 a monetary amount, i.e., and initial funding amount, with which to fund a newly created TAA. The amount may exceed the cost of the qualified expense, be equal to the cost of the qualified expense, or be less than the qualified expense. Funding subsystem 214 may further receive a designated account, e.g., a savings, checking, or credit card account or other suitable source, from which to receive the initial funding amount. Funding subsystem 214 may receive this information through a web service request or via interface 230, i.e., via a web-interface and one or more servers processing web-based traffic and HTTP request methods.

In one embodiment, funding subsystem 214 may allow peer-to-peer transactions to be conducted within the Retail HSA process. Funding subsystem 214 may employ a custodial account to hold funds in escrow while engaging ACH funding processes, wire transfers, or other payment mechanisms to complete the transfers. In another embodiment, funding subsystem 214 may employ an external service to complete peer-to-peer transactions in real-time or near-real time. Thus to stakeholders, e.g., a prospective account holder and the provider at a point of sale, the funding mechanism employed by funding subsystem 214 upon account creation functions in real-time or near-real time. While legacy systems employ ACH transactions or use other trusted intermediaries to complete transactions, which causes a lapse in time between when funds are deposited and made available to the account holder, funding subsystem 214 allows the Retail HSA process to create and immediately fund the TAA and subsequently and immediately pay a provider from the funded TAA. Funding subsystem 214 may provide suitable APIs that receive web-service requests that create accounts, process transactions, and interact with other subsystems in system 100. When initially funding a TAA, funding subsystem 214 may create a tracking value corresponding to the initial contribution amount to be received from a linked bank account and a second tracking value corresponding to the amount to the transferred from the TAA to the provider system. These tracking values may be encrypted using appropriate security methods to assure the subsystems that the transactions are secured. Funding subsystem 214 may lock the funds related to the initial contribution until completion of the payment to the provider to avoid double-spending and assure the provider that the transaction will be completed.

Transaction manager 215 may manage transactions received from any of the subsystems described with reference to FIG. 1. Transaction manager 215 may generate bank transactions to create new TAAs, fund the TAAs, and render payment to a provider of a qualified expense. Transaction manager 215 may store both the received transactions and generated transactions in management transaction log 228. As part of creating and funding accounts across the multiple systems of FIG. 1, transaction manager 215 may send a generated bank transaction to transaction manager 312 in bank system 106 or to transaction manager 412 in provider system 108.

Record generation subsystem 216 may generate records of transactions, account creations, and payments of qualified expenses. Record generation subsystem 216 may create PDFs, DOCs, HTML documents, or other documents for downloading and viewing. Record generation subsystem 216 may pull requisite information from management database 220 using, for example, appropriately formatted SQL queries and subsequently use a typesetting program, PDF or document generation module, other suitable method to generate documentation.

Over-contribution subsystem 217 may analyze linked TAAs to detect over-contributions and alert account holders about potential over-contributions. Over-contribution subsystem 217 may alert a prospective or current account holder of any over-contributions and provide procedural options to remedy the defect, e.g., to render payment from an existing TAA, reduce the initial contribution amount, etc. Over-contribution subsystem 217 may be engaged by management system 200 in the initial creation and funding of the TAA that occurs during the Retail HSA process. In another embodiment, over-contribution subsystem 217 may be called by an account holder using management UI portal 211 at any time during a plan year.

Retroactive analysis subsystem 218 may perform retroactive analysis of linked bank accounts to determine qualified expenses that occurred previously. Retroactive analysis subsystem 218 may perform the retroactive analysis during the creation and funding of TAA in the Retail HSA system. In another embodiment, an account holder may trigger retroactive analysis on an ad-hoc basis through management UI portal 211. Retroactive analysis subsystem 218 may identify eligible transactions in the linked accounts and create tax-eligible transactions in the newly created TAA representing the eligible transactions that occurred previously in a plan year. Retroactive analysis subsystem 218 may allow account holders to confirm the eligibility of the transaction and to enter an eligible portion, i.e., a portion of the total amount of the transaction that is a qualified expense. Retroactive analysis subsystem 218 may determine an aggregate contribution amount based on the eligible portions entered across all eligible transactions. Retroactive analysis subsystem 218 may then deposit an amount corresponding to the aggregate contribution amount into the TAA and then immediately withdraw the same amount from the TAA thus creating a qualified expense for the plan year in the amount of the aggregate contribution amount. In another embodiment, retroactive analysis subsystem 218 may complete deposits/withdrawals for each identified eligible portion, as opposed to one deposit/withdrawal for the aggregate amount. Retroactive analysis subsystem 218 may engage a peer-to-peer payment mechanism to complete the transactions or other suitable payment mechanism.

Management database 220 may store information about account holders and other system features in one or more of the following database tables: user tables 221, configuration tables 225, management transaction log 228, and valid providers 229. User tables may include user information 222, bank accounts 223, and linked accounts 224. Configuration tables 225 may include MP table configurations 225 and sequence selectors 227. Management database 220 may store records and information related to management system 200 in any commercially available database management system or open-source solution. Management database 220 may maintain communicative connections via traditional networking infrastructure such as routers, switches, hubs, firewalls, etc.

User tables 221 may store account holders' information including benefit plan, account information, account balances, account settings and customizations, user demographic information, transaction history, etc. User tables 221 may include user information 222, bank accounts 223, and linked accounts 224.

User information 222 may include user-identifying information, e.g., full name, date of birth, address, phone number, email address, other contact information, social security number, and other suitable demographic information. User information 222 may also include census information, salary, employment status, associated employer, contribution amounts, and other suitable user information. User information 222 may further include investment information describing the proportion of funds within TAAs or other bank accounts. User information 222 may further include encrypted login/password combinations or other security-related information.

Bank accounts 223 may store information about bank accounts for account holders represented in user information 222. Point-of-sale terminal 110 may transmit the bank account information to management system 102 for storage in bank accounts 223 when initially creating accounts for the prospective account holder. Bank accounts 223 may include account numbers, routing numbers, user names, financial institution information, and other account identifiers.

Linked accounts 224 may store information about linked accounts for account holders represented in user information 222. Linked accounts 224 may include one or more TAAs held by an account holder as well as savings, checking, credit, and other bank accounts. The account holder may manage these accounts in an individual capacity or other plan managers may manage the accounts. Linked accounts 224 may link other TAAs to allow management system 200 to perform over-contribution analysis. Linked accounts 224 may also include bank accounts stored in bank accounts 223, for example, if an account holder links a bank account to allow management system 200 to perform retroactive analysis.

Configuration tables 225 may store configurations for account holders and their accounts. Configuration tables 225 may store information relevant to a hierarchical-payment-account configuration that management system 102 receives when creating the TAA at the point of sale. Configuration tables 225 may include MP table configurations 226 and sequence selectors 227.

MP table configuration 226 may include MP-table configurations selected or configured that specify a hierarchical-payment-account configuration. An MP-table configuration may be a data structure representing the TAAs, bank accounts, credit accounts, etc., selected for a benefit plan, and may represent various rules and restrictions associated with the accounts.

Sequence selectors 227 may store claims processing sequences for the account holder. A processing sequence may include a prioritized list of account identifiers, each account ID associated with a corresponding TAA, bank account, credit card, etc. The processing sequence may include a prioritized list of all possible account identifiers corresponding to all possible accounts provided within bank accounts 223.

Management transaction log 228 may store records of generated and received transactions. Transaction records may include records of banking transactions, account creations, and other activities of management system 200. As part of creating TAAs and generating transactions for the TAAs across the multiple systems of FIG. 1, management transaction log 228 may store generated bank transactions to/from transaction manager 304 in bank system 106 and to/from transaction manager 412 in provider system 108.

Valid providers 229 may be a table of providers in management system 200. Retroactive analysis subsystem 218 may use valid providers 229 to determine eligible transactions that an account holder previously completed in a plan year during the retroactive analysis process. Valid providers 229 may be accrued over time by management server 210 as management system 200 processes claims, e.g., when a claim processing component validates a claim, the provider may be added to valid providers 229. Valid providers 229 may include a terminal identifier, a location identifier, and name. In an embodiment, valid providers 229 may also include a classification of a provider's business product or service, an authorization identification response used when a transaction occurs at the provider, a unique code identifying a terminal at the provider, a unique code identifying a card acceptor, and a name-location pair identifying a point of service. Thus, retroactive analysis subsystem 218 may employ Valid providers 229 to determine qualified expenditures provided by eligible providers.

Interface 230 may enable management system 200 to communicate with one or more subsystems across system 100. Though depicted as a separate component, interface 230 may be implemented within management server 210, according to an example embodiment. Interface 230 may allow system 100 to update, modify, and otherwise configure the information in management system 200. Interface 230 may provide a web-interface to achieve this functionality, i.e., one or more servers processing web-based traffic and HTTP request methods. Interface 230 may process web-traffic, HTTP request methods, web service requests (e.g., XML, SOAP, USDL, or UDDI) from system 100. Interface 230 may accept a username token, security token, public key, etc. to establish a trusted connection or use another method of determining the identity of the requester. Interface 230 may deploy a standard web server technology to listen for, process, and respond to any of these incoming hits/requests. Interface 230 may return pages via HTTP, which interface 230 formulates in accordance with hypertext transfer protocol W3C standards. The returned pages may also include images, stylesheets, and scripts, the content and nature of which will be appreciated by those skilled in the relevant art(s). Interface 230 may specifically format the responses for viewing on a mobile device in adherence with W3C mobile web best practices. In some embodiments, management system 200 may respond to web service requests received from one system in system 100 and subsequently send a web service request to another system in system 100.

Figure 3:
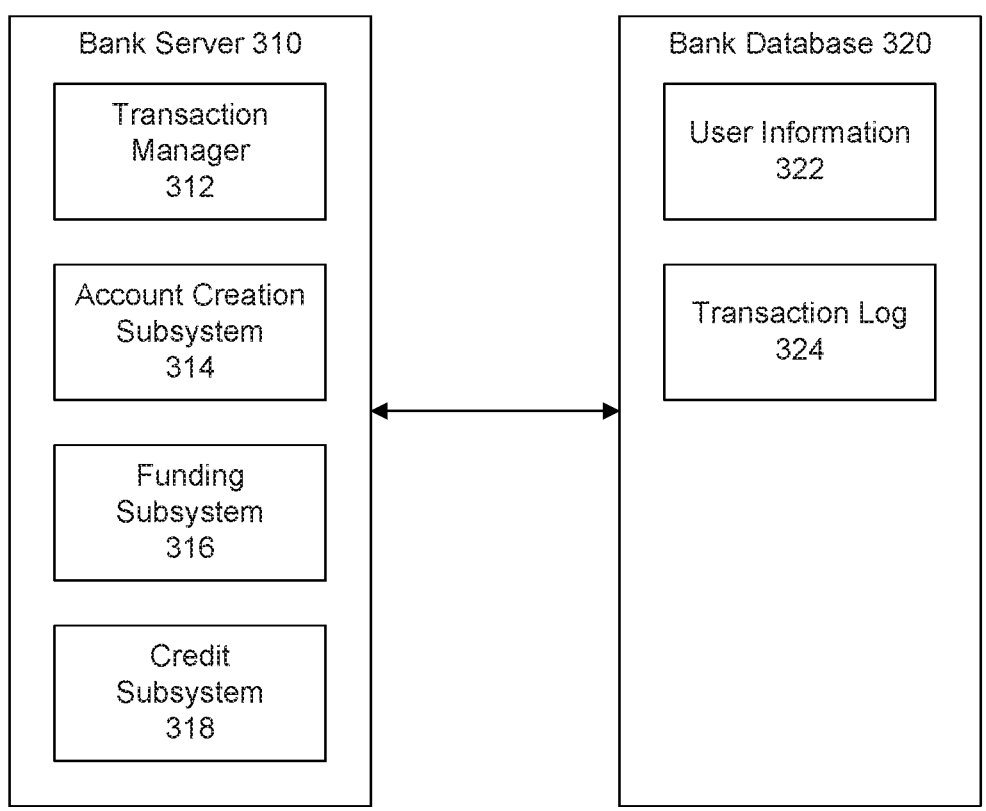
FIG. 3 is an example block diagram illustrating a bank system, according to an example embodiment.

FIG. 3 is an example block diagram illustrating bank system 300, according to an example embodiment. Bank system 300 may be an embodiment of bank system 106 of FIG. 1. Bank system 300 may include bank server 310 and bank database 320. Though depicted as a single server, bank server 310 may represent a plurality of servers, each of which may be implemented by one or more processors. Likewise, bank database 320 may represent a plurality of databases coupled to a plurality of bank servers. Additionally, one or more of the depicted components may be implemented as processing systems comprising one or more sub-components. These sub-components may include an interface for communicating within and/or across systems and a distribution component for sending information to other components and/or across systems.

Bank server 310 may include transaction manager 312, account creation subsystem 314, funding subsystem 316, and credit subsystem 318. Bank server 310 may provide a web-interface to achieve this functionality, such as one or more servers processing web-based traffic and HTTP request methods. Bank server 310 may process web-traffic, HTTP request methods, web service requests (e.g., XML, SOAP, USDL, or UDDI) from subsystems in system 100. Bank server 310 may deploy a standard web server technology to listen for, process, and respond to any of these incoming hits/requests. In some embodiments, bank server 310 may respond to web service requests received from one system in system 100 and subsequently send a web service request to another system in system 100.

Transaction manager 312 may process transactions received from one or more of the systems or computers depicted in FIG. 1 as would be understood by one skilled in the art(s). Transaction manager 312 may receive transactions generated by transaction manager 215 in management system 200 for account creation and funding and rendering of payment for a qualified expense as described in FIG. 2 and further described in FIGS. 6-7. Transaction manager 312 may also receive transactions generated by transaction manager 412 in provider system 400 for account creation and funding and rendering of payment for a qualified expense.

Account creation subsystem 314 may communicate with creation subsystem 213 in management system 200 to create new account information in bank database 320, and to fund that account via transaction manager 312. For example, account creation subsystem 314 may receive a request from point-of-sale terminal 110 to open and fund a TAA and to cover the qualified expenditure amount from the newly created TAA. Accordingly, account creation subsystem 314 may update records stored in bank database 320 to reflect the newly created account. Account creation subsystem may add or insert records into user information 322.

Funding subsystem 316 may receive funds related to provided qualified expenses. Funding subsystem 316 may include information regarding bank accounts, debit accounts, credit accounts, and other fund receiving mechanisms. Funding subsystem 316 may provide account numbers, routing numbers, and/or other payment device information upon request to send and receive funds.

Credit subsystem 318 may provide lending options used by management system 200 when providing a credit feature in the Retail HSA process. Credit subsystem 318 may extend services accessible via API calls conducted during the account creation and funding process that offer various terms, conditions, rates, etc. related to crediting options providing by bank system 300. For example, credit subsystem 318 may alert management server 210 that a particular account holder may receive $5,000 in credit including an appropriate interest rate, terms, and other conditions. Credit subsystem 318 may further receive a confirmation of the acceptance of the terms and interact with funding subsystem 214 to fund the account during the creation process. Although credit subsystem 318 is displayed in FIG. 3 as being contained within bank server 310, in other embodiments, credit subsystem 318 may be independent from bank server 310 or a bank entirely, e.g., an independent lending institution may provide and expose the service/API to provide the functions performed by credit subsystem 318.

Bank database 320 may store user information 322 and transaction log 324 in one or more database tables. Bank database 320 may store records and information related to bank system 300 in any commercially available database management system. Bank database 320 may maintain communicative connections via traditional networking infrastructure such as routers, switches, hubs, firewalls, etc.

User information 322 may store identifying personal information for account holders or prospective account holders. User information 322 may include identifying information, such as and without limitation full name, date of birth, address, phone number, email address, other contact information, social security number, and other suitable demographic information. User information 322 may further store encrypted login/password information used to verify the users' identities.

Transaction log 324 may store and maintain transaction logs. For example, transaction manager 312 may receive such transactions from transaction manager 215 within management system 200. Transaction log 324 may store sufficient documentation to support and validate the transaction.

Figure 4:
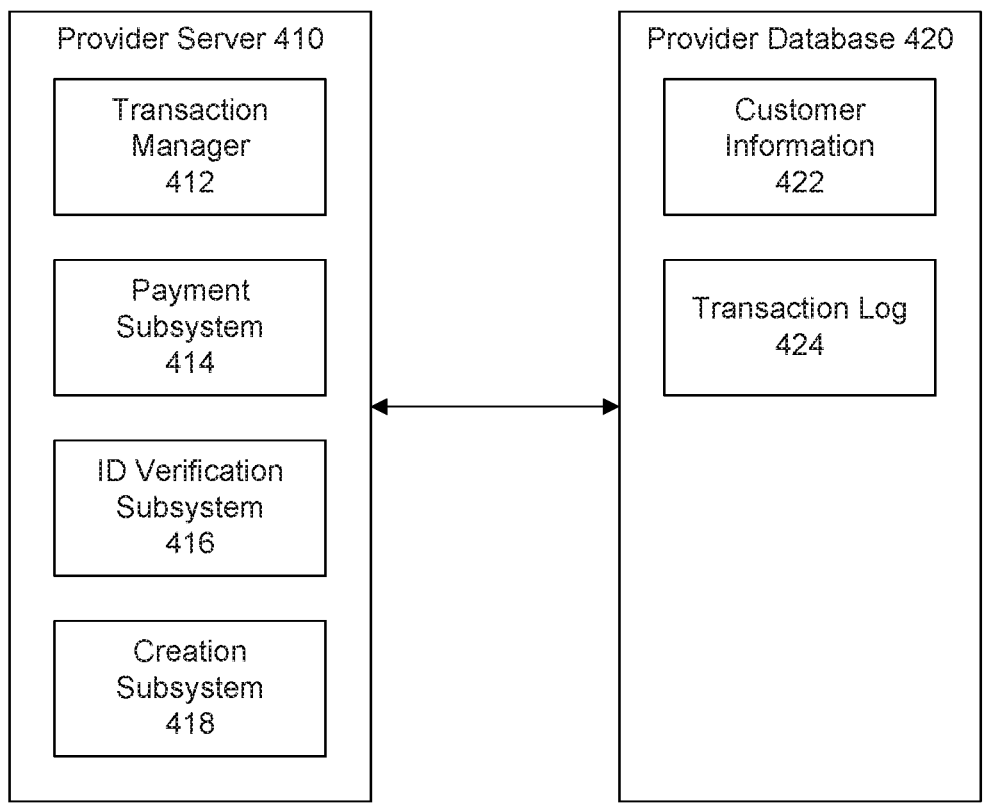
FIG. 4 is an example block diagram illustrating a provider system, according to an example embodiment.

FIG. 4 is an example block diagram illustrating provider system 400, according to an example embodiment. Provider system 400 may be an embodiment of provider system 108 of FIG. 1. Provider system 400 may include provider server 410 and provider database 420. Though depicted as a single server, provider server 410 may represent a plurality of servers, each of which may be implemented by one or more processors. Likewise, provider database 420 may represent a plurality of databases coupled to a plurality of provider servers. Additionally, one or more of the depicted components may be implemented as processing systems comprising one or more sub-components. These sub-components may include an interface for communicating within and/or across systems and a distribution component for sending information to other components and/or across systems.

Provider server 410 may include transaction manager 412, payment subsystem 414, identity verification subsystem 416, and creation subsystem 418. Provider server 410 may provide a web interface to achieve this functionality, i.e., one or more servers processing web-based traffic and HTTP request methods. Provider server 410 may process web-based traffic, HTTP request methods, or web service requests (e.g., WL, SOAP, USDL, or UDDI) from across system 100. Provider server 410 may deploy a standard web server technology to listen for, process, and respond to any of these incoming hits/requests. In one embodiment, provider server 410 and point-of-sale terminal 110 may reside on a single server but may also be a plurality of servers that connect through a suitable network connection.

Transaction manager 412 may process transactions received from one or more of the systems or computers depicted in FIG. 1, as would be understood by one skilled in the art. Transaction manager 412 may generate and send banking transactions to transaction manager 215 of management system 200, transaction manager 312 of bank system 300, or to a qualified electronic transaction clearing house to fund a TAA and receive payment of a qualified expense therefrom.

Payment subsystem 414 may send billing information to transaction manager 215 of management system 200. Payment subsystem 414 may receive appropriate funding to cover a qualified expense from funding subsystem 316 of bank system 300. Payment subsystem 414 may include an account number and/or routing number for receiving payments to cover services provided.

Identity verification subsystem 416 may send an identity verification request to management system 102. Identity verification subsystem 416 may require an on-site representative to verify a qualified issued identification source. Identity verification subsystem 416 may send a web service request to a qualified identity verification agent and receive in return an identity verification response. Identity verification subsystem 416 may communicate via network transmissions with identification subsystem 212 of management system 200 described in FIG. 2.

Creation subsystem 418 may create account information for the prospective account holder in provider system 400. Creation subsystem 418 may use identifying information, e.g., full name, social security number, etc., to uniquely identify the prospective account holder with provider system 400. Creation subsystem 418 may receive additional information about the prospective account holder including: credit card accounts, debit accounts, other funding sources, etc., for prioritizing into a hierarchical account structure at the time of account creation. Creation subsystem 418 may store information about the account holder in provider database 420.

Provider database 420 may include customer information 422 and transaction log 424. Provider database 420 may store customer information 422 and transaction log 424 via one or more database tables. Provider database 420 may store records and information related to provider system 400 in any commercially available database management system. Provider database 420 may maintain communicative connections via traditional networking infrastructure such as routers, switches, hubs, firewalls, etc.

Customer information 422 may include identifying personal information related to the customer's association with and purchases from the provider. Customer information 422 may include identifying personal information for customers, such as and without limitation, full name, date of birth, address, phone number, email address, other contact information, social security number, and other suitable demographic information. Customer information 422 may further include preferences, settings, internal identification numbers, appointment information, medical history, or any other suitable information pertinent to provider system 400.

Transaction log 424 may store and maintain records of banking transactions, account creations, and other occurrences in provider system 400. For example, transaction manager 215 within management system 200 may receive these transactions from transaction manager 312 or transaction manager 412.

Figure 5:
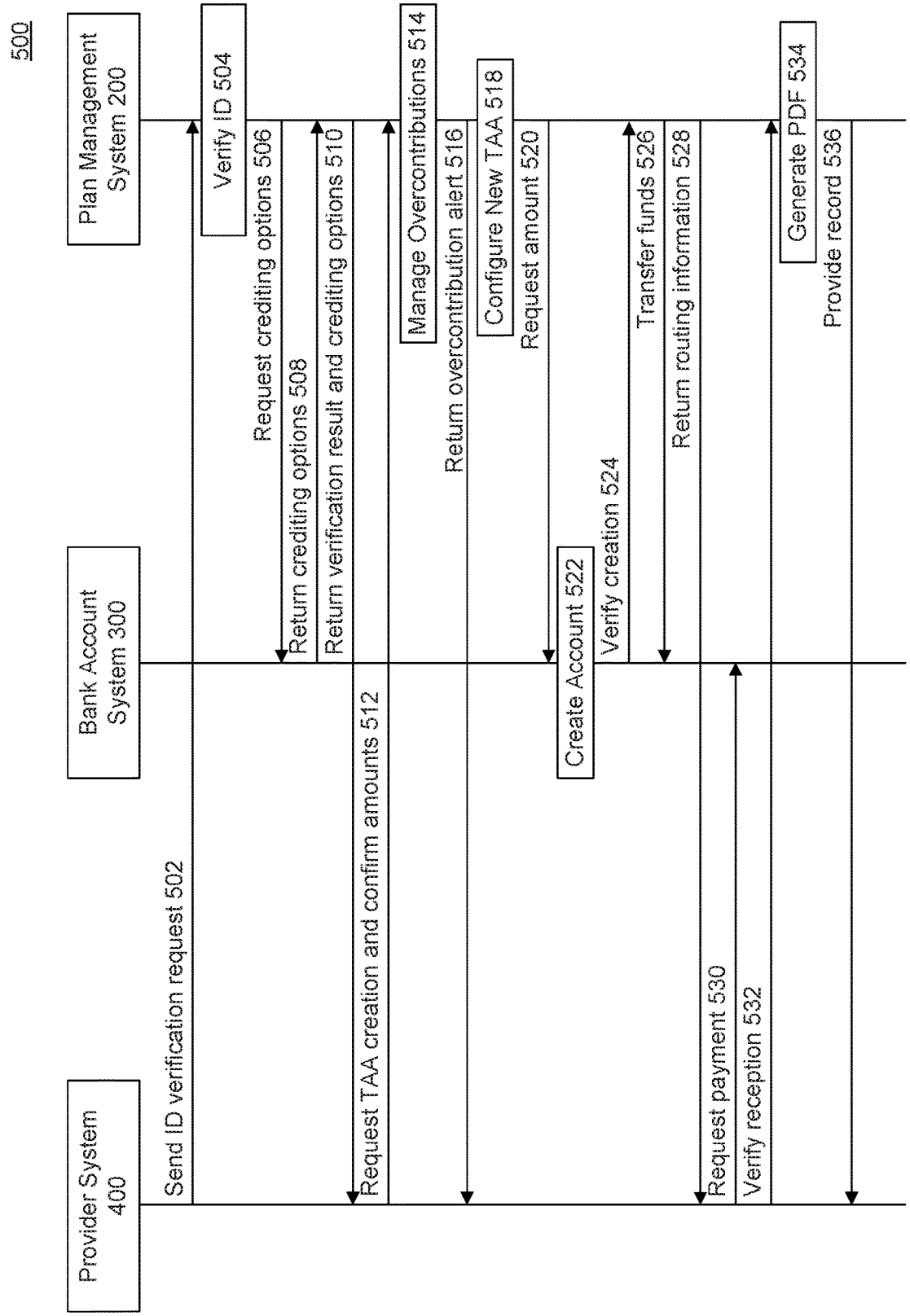
FIG. 5 is a flowchart illustrating steps for creating and funding a TAA at a point of sale and for rendering payment to the provider of a qualified expense from the newly created TAA, according to an example embodiment.

FIG. 5 illustrates a method 500 for creating and funding a TAA at a point of sale and for rendering payment to the provider of a qualified expense from the newly created TAA, according to an example embodiment. Method 500 may commence at the point of sale of a qualified expense when the recipient elects to create and fund a TAA at the point of sale. Subsequently, the TAA renders payment to the provider of the qualified expense from the TAA. Method 500 may be performed by processing logic that may include hardware (e.g., circuitry, dedicated logic, programmable logic, microcode, etc.), software (e.g., instructions run on a processing device), or a combination thereof. In an embodiment, some steps in FIG. 5 may not need to be performed in the exact order shown as one skilled in the art would understand.

In step 502, identity verification subsystem 416 of provider system 400 may send an identification verification request to management system 200 for a prospective account holder. Identity verification subsystem 416 may receive requisite data in forms generated and provided via HTTP, formulated in accordance with hypertext transfer protocol W3C standards. In an alternate embodiment, identification subsystem 212 of management system 200 or interface 230 may serve appropriate forms and webpages to receive data from provider system 400. Management system 200 may specifically format the responses for viewing on a mobile device in adherence with W3C mobile web best practices so that the available rewards may be viewed via communication interfaces. In an alternate embodiment, interface 230 may process web service requests (e.g., XML, SOAP, USDL, or UDDI) from provider system 400. The verification request may also include an amount or cost related to a qualified expense provided at the point of sale.

In step 504, identification subsystem 212 of management system 200 may receive the identification request and verify the identity of the prospective account holder. The user-identifying information may include, for example and without limitation, a full name, date of birth, social security or other identifying number, and/or other suitable information. Identification subsystem 212 may receive this data as text, JSON, XML, HTML, or other human readable format or appropriate machine readable format. Identification subsystem 212 may further require an on-site identity check through manual or electronic validation and confirmation of a state identification card, social security card, passport, or other qualifying method of manual identification verification. In such an embodiment, management system 200 may receive a further transmission from provider system 400 confirming that manual validation of identification occurred. Identification subsystem 212 may send an appropriately formatted web service request or other suitable transmission to an independent identification verification organization to verify an individual's identity to create a TAA. In response, identification subsystem 212 may receive an appropriately formatted response, e.g. XML or other suitable format, indicating the success or failure of the independent identification verification. In alternate embodiments, plan management system 200 may contact an independent identification verification organization through other suitable communication methods, or management system 200 may perform the verification of the prospective account holder internally within identification subsystem 212.

In step 506, identification subsystem 212 of management system 200 may return a verification result to provider system 400, depending on the outcome of step 504. The verification may be a successful verification of the identity of the prospective account holder to start and fund a TAA, an inability to verify identity, a failed or unsuccessful transmission/response, etc. Identification subsystem 212 may provide the verification result via appropriate HTML web pages, i.e. in forms and pages generated and provided via HTTP or other suitable protocol, or identification subsystem 212 may return the results via web service request or other suitable transmission.

In 508, a prospective account holder may request crediting options via point-of-sale terminal 110 or provider system 400. Such a prospective account holder may lack sufficient means to specify an account from which to fund a TAA to the amount necessary to cover the initial funding amount and/or the cost of the qualified expense. Plan management system 200 may determine various terms, conditions, rates, etc. related to crediting options to satisfy the amount needed. In an embodiment, plan management system 200 may access credit subsystem 318 to retrieve suitable credit options offered by a bank or creditor to finance the amount requested by the prospective account holder. The amount requested may be the initial funding amount, the amount to be paid to the provider, or another suitable amount.

In 510, management system 200 may return the crediting options to the account holder. In an embodiment, management system 200 may request available lending options from multiple lenders, i.e., multiple interfaces such as credit subsystem 318, and present the multiple options to the account holder for selection and acceptance. Although credit subsystem 318 is displayed in FIG. 3 as being contained within bank server 310, in other embodiments, credit subsystem 318 may be independent from bank server 310 or a bank entirely, e.g., an independent lending institution may provide and expose the service/API to provide the functions performed by credit subsystem 318. In another embodiment, management system 200 may determine the most suitable crediting options algorithmically by analyzing the rates, terms, and conditions of the returned crediting options.

In step 512, management system 200 may receive a confirmation of the TAA creation request, a confirmed initial funding amount, and an assent to the terms of a crediting option, if applicable. Creation subsystem 213 may receive further information about the account(s) to create, the prospective account holder, and any lending options. This information may include, for example: bank or credit card account information for the prospective account holder, MP configuration information, the cost of the qualified expense, the total amount of funds with which to fund the new TAA (which may be greater than, equal to, or less than the cost of the qualified expense), and other suitable information about the prospective account holder, the new TAA, and/or the qualified expense. Similar to step 502, creation subsystem 418 may submit the information via HTTP or other suitable protocol, leverage web service requests, or use another suitable approach.

In 514, over-contribution subsystem 217 may perform an over-contribution analysis. For example, over-contribution subsystem 217 may analyze linked TAAs, a TAA balance, and an initial contribution amount to detect over-contributions. Management system 200 may engage over-contribution subsystem 217 in the initial creation and funding of the TAA that occurs during the Retail HSA process. In another embodiment, management system 200 may engage over-contribution subsystem 217 in response to an ad-hoc request from an account holder or at other suitable times. This process of performing an over-contribution analysis is described in further detail below with reference to FIG. 10.

In 516, over-contribution subsystem 217 may return an over-contribution alert to the account holder. For example, the alert may inform the account holder about the determined aggregate contribution amount for the plan year, list the contributions across the TAAs, and display other suitable information. Over-contribution subsystem 217 may provide procedural options to remedy the defect, e.g., to render payment from an existing TAA, reduce the initial contribution amount, etc. Method 500 may continue to step 518 when the account holder resolves any potential over-contribution alert satisfactorily.

In step 518, creation subsystem 213 of management system 200 may create and configure a new TAA for the prospective account holder. Creation subsystem 213 may create and/or insert new records into user tables 221 to add records of the prospective account holder to management system 200. Creation subsystem 213 may further update existing records if the prospective account holder already exists in some alternate capacity in user tables 221, e.g., if management system 200 tracks the prospective account holder's retirement accounts IRA but not the type of TAA being created. In addition to updating/inserting information into user information 222, creation subsystem 213 may add records corresponding to the received bank accounts from provider system 400 to bank accounts 223. Creation subsystem 213 may further update configuration tables 225 when the prospective account holder simultaneously configures a hierarchy of payment accounts in management system 200. Creation subsystem 213 may also add records to MP table configuration 226 and sequence selectors 227. Creation subsystem 213 may record the creation of the accounts as a transaction in management transaction log 228.

In step 520, creation subsystem 213 of management system 200 may request the creation of one or more accounts with account creation subsystem 314 of bank system 300. Creation subsystem 213 may transmit requisite information to account creation subsystem 314 to open the TAA. The information may include, for example and without limitation: account type(s), first name, middle name, last name, email address, phone numbers, social security number, name of employer, address, identity verification garnered in step 504, and/or any other suitable or required information.

In step 522, account creation subsystem 314 of bank system 300 may create an account to serve as the balance for the TAA. Account creation subsystem 314 may provide a web interface to receive web transmissions allowing the automatic creation of the TAA. Account creation subsystem 314 may perform additional identity verification services. Account creation subsystem 314 may receive this data as text, JSON, XML, HTML, or other human-readable format or appropriate machine-readable format. Account creation subsystem 314 may formulate appropriate queries and receive results by running these queries on bank database 320. Account creation subsystem 314 may assign an American Bankers Association (ABA)/routing number, transit number, and/or account number for use in banking transactions such as electronic fund transfers, deposits, bill payments, tax payments, etc. Account creation subsystem 314 may use the transferred funds to initially fund the created account.

In step 524, account creation subsystem 314 of bank system 300 may return verification of the account creation to funding subsystem 214 of management system 200, depending on the occurrences in step 518. Account creation subsystem 314 may transmit this data as text, JSON, XML, HTML, or other human readable format or appropriate machine-readable format to funding subsystem 214. The verification may indicate a successful creation of the account or denote an unsuccessful account creation. The verification may further include the ABA number, transit number, and/or account number for the newly created TAA, which plan management system 200 may subsequently access. Such a verification may indicate a successful creation of the TAA and a further confirmation that the TAA received the initial amount of funds in the TAA as requested in step 508. The verification may include an account number and an ABA number or other routing number reflecting the newly created, funded TAA as received in step 518.

In step 526, funding subsystem 214 of management system 200 may transfer the requisite amount of funds to funding subsystem 316 of bank system 300 using a peer-to-peer funding mechanism. Funding subsystem 214 may use the bank or credit card account information for the prospective account holder received in step 508 as the source account of the formulated banking transaction. Funding subsystem 214 may use the amount requested in step 508 as the transfer amount. Funding subsystem 316 of bank system 300 may verify a successful funding of the TAA to management system 200.

In step 528, funding subsystem 214 may return routing information to payment subsystem 414 in provider system 400. This routing information may include one or more tracking numbers and a confirmation that the bank account locked the funds to avoid a double-spend.

In step 530, payment subsystem 414 of provider system 400 may request payment of the qualified expense from transaction manager 312 of bank system 300. In an alternate embodiment, transaction manager 215 of plan management system 200 may perform step 530. In an embodiment, payment subsystem 414 (or in an alternate embodiment, transaction manager 215) may generate an appropriate banking transaction for processing by an automatic clearinghouse. The source account may be the newly created TAA reflected in the routing number and account number received in step 528. The destination account may be a bank account and/or routing number or an alternate provider payment method determined by payment subsystem 414. One skilled in the art(s) will appreciate that the amount of the qualified expense may be less than the initial funding amount determined by the account holder in step 512. In this case, the TAA may retain a balance after step 530 completes. Similarly, the qualified expense may exceed than the initial funding amount (perhaps because the qualified expense is greater than the allowable initial contribution amount of the TAA). In this case, provider system 400 may seek a remaining balance from the account holder via an alternative payment method, e.g., by a receiving a check or cash at the point of sale.

In step 532, creation subsystem 418 of provider system 400 may verify the fund transfer from the newly created TAA to provider subsystem 414. Similar to step 502, creation subsystem 418 may submit the information via HTTP, HTTPS, other web service requests, or using another suitable approach. The information may include information relevant to the transaction and a record-generation request flag.

In step 534, record generation subsystem 216 of management system 200 may generate an appropriate record of the transaction. Record generation subsystem 216 may generate a record of the transaction and store it in management transaction log 228. In addition to generating a record of the transaction and storing the record in management database 220, record generation subsystem 216 may create a PDF, image file, or other suitable MIME type file and store the file, for example on a NAS, SAN, local hard drive, or other suitable storage mechanism, to serve later via HTTP or other suitable protocol.

In step 536, management UI portal of management system 200 may make available to provider system 400 the recordkeeping document generated in 526. Management UI portal 211 may serve such a document to the account holder or a representative at provider system 400. Record generation is discussed in further detail below with reference to FIG. 7.

Figure 6:
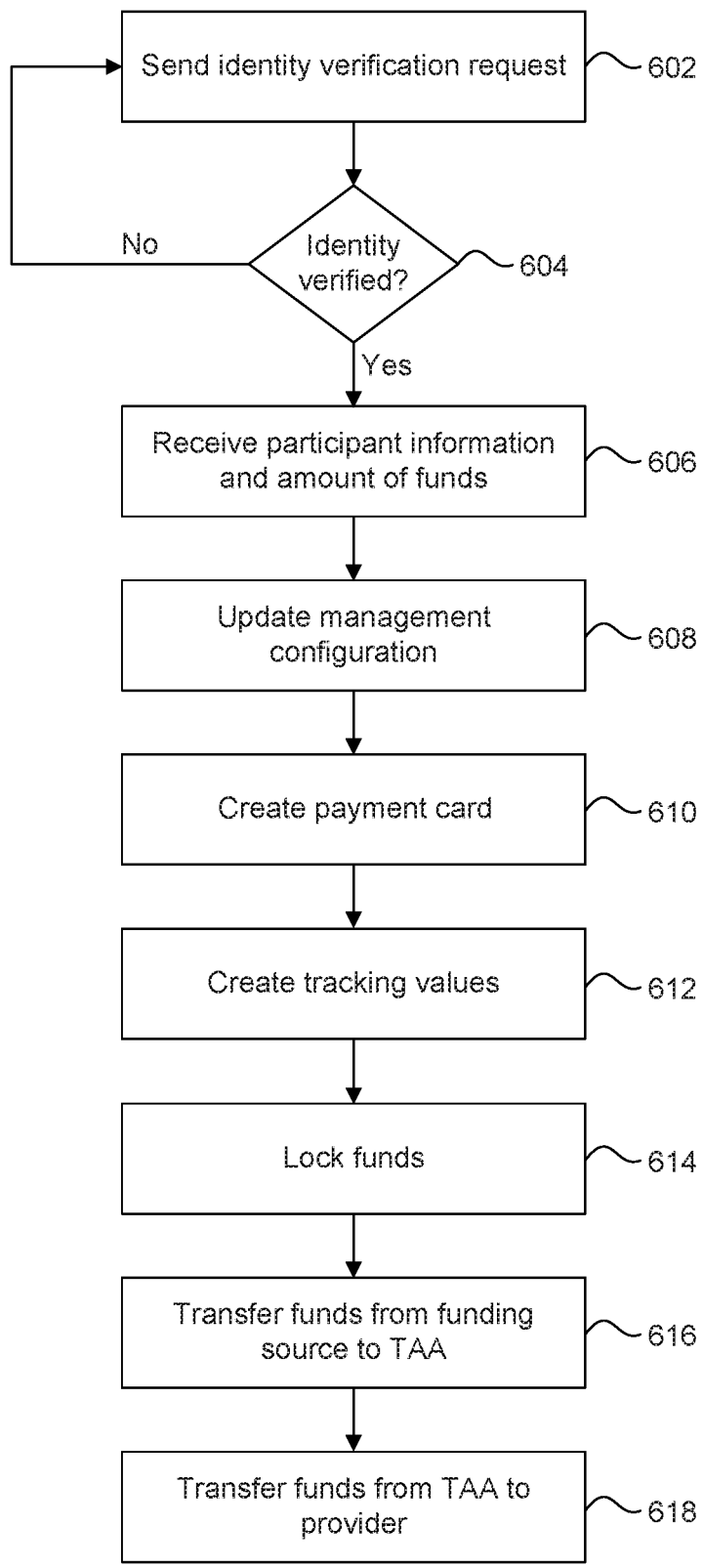
FIG. 6 is a flowchart illustrating a process of verifying an account holder's identity at a point of sale, creating and funding a TAA, and immediately paying a provider from the TAA, according to an example embodiment.

FIG. 6 illustrates a method 600 illustrating a process of verifying an account holder's identity at a point of sale, creating and funding a TAA, and immediately paying a provider from the TAA, according to an example embodiment. Method 600 may be performed by processing logic that may include hardware (e.g., circuitry, dedicated logic, programmable logic, microcode, etc.), software (e.g., instructions run on a processing device), or a combination thereof. In an embodiment, some steps in FIG. 6 may not need to be performed in the exact order shown as one skilled in the art(s) would understand.

In step 602, identification subsystem 212 of management system 200 may send a verification request to a qualified identity verification agent. Identification subsystem 212 may transmit text, JSON, XML, HTML, or other human-readable format or an appropriate machine-readable format. Identification subsystem 212 may include, for example and without limitation, a full name, date of birth, social security or other identifying number, and any other suitable information. In response, identification subsystem 212 may receive an appropriately formatted response, e.g. XML or other suitable format, indicating the success or failure of the independent identification verification. In alternate embodiments, plan management system 200 may contact an independent identification verification organization via suitable communication methods, or management system 200 may perform the verification of the prospective account holder internally within identification subsystem 212. In another embodiment, identification subsystem 212 may receive confirmation of a prior conducted identity verification from identity verification subsystem 416 of provider system 400.

In step 604, identification subsystem of management system 200 determines if identification subsystem 212 verified the identity of the prospective account holder in step 602. If not, then method 600 returns to step 602. If identification subsystem 212 verified the prospective account holder's identity, then method 600 proceeds to step 606.

In step 606, creation subsystem 213 of management system 200 may receive or retrieve additional information about the prospective account holder and the TAA. Information about the TAA may include an amount of funds authorized by the prospective account holder with which to initially fund the TAA and a funding account from which to draw the initial funding amount. The information may further include demographic information about the prospective account holder including date of birth, first name, middle name, last name, email address, phone numbers, social security number, name of employer, address, identity verification data garnered in step 602, and any other suitable or required information. In an embodiment, creation subsystem 213 may also receive information about linked bank accounts, credit card accounts, or debit accounts, and the account holder may specify a funding source from which a created TAA may be initially funded from among the linked accounts. Creation subsystem 213 may also receive management plan configuration selections (e.g., a multi-purse configuration) and any other suitable information about the potential account holder to be used in management system 200.

In step 608, creation subsystem 213 may update/create appropriate structures in management database 220 based on the information received in step 606 and/or from provider system 108. Creation subsystem 213 may create a TAA associated with a TAA balance. Creation subsystem 213 may link specified bank accounts, including the initial funding source specified by the prospective account holder, with the TAA. Creation subsystem 213 may also update user tables 221 by adding the prospective account holder's identifying information to user information 222. Creation subsystem 213 may further update bank accounts 223 to include savings, debit, credit, and other bank accounts received in step 606. Creation subsystem 213 may formulate and execute appropriate insert/update queries and execute these queries against management database 220.

In step 610, funding subsystem 214 may create and initialize a payment card including a card number, an expiration date, a Card Verification Value ("cvv"), and other appropriate information. The payment card may be used to authorize transactions, including those that occur in the Retail HSA process during the initial funding of the account and immediate rendering of payment. Funding subsystem 214 may associate the payment card with the new TAA created in step 608. In an embodiment, the account holder may receive a physical representation of the payment card at a later time.

In 612, funding subsystem 214 may create tracking values to catalog and track the transfers to be conducted during the retail HSA process. By creating the transactions and tracking the transactions using the tracking values and the newly created payment card number, funding subsystem 214 may avoid a lapse in fund availability existing in legacy systems. By eliminating this lapse, funding subsystem 214 may concurrently create and fund a TAA and then immediately render payment from the newly created TAA to the provider. Funding subsystem 214 may create a first tracking value corresponding to the initial contribution amount to be received, i.e., deposited into the TAA balance, from the specified initial funding source. Funding subsystem 214 may create a second tracking value corresponding to the amount to be transferred from the TAA balance using the payment card number to a provider system to pay for a qualified expense. Additional tracking numbers and data may be created by funding subsystem 214 to ensure the occurrence of appropriate transactions and secure the system against double-spending and other attempts to defraud the system.

In 614, funding subsystem 214 may lock the funds corresponding to the initial contribution amount at the specified funding source until the retail HSA process completes, i.e., the provider receives payment for the qualified expense. Funding subsystem 214 may also send a confirmation to provider system 400 that includes the tracking value, the payment card number, and other identifying information. This lock and confirmation creates a trust relationship between the provider and management system 200 and confirms that the funds will arrive at a bank account associated with the provider.

In 616, funding subsystem 214 may transfer the initial funding amount from the funding account to the TAA balance. Funding subsystem 214 may employ a funding source specified by the account holder as the funding source from which to draw the initial funding amount. Funding subsystem 213 may create a peer-to-peer transaction to immediately fund the TAA using the first tracking number generated in 612 and other information associated with the funding source and the TAA created in 608. In another embodiment, funding subsystem 214 may employ an ABA number, transit number, routing number, and/or account number for the TAA or use an electronic fund transfer service or automatic clearing house to conduct the transaction. In either embodiment, the TAA balance receives the initial funding amount from the funding source specified by the account holder, and these funds are immediately available for use in the subsequent steps and to complete additional transactions.

In 618, funding system 214 may immediately transfer the expenditure amount from the TAA balance to a provider account associated with the provider using the payment card number generated in 610. Funding subsystem 214 may employ the newly created TAA as the source account for the transfer. Funding subsystem 213 may employ a peer-to-peer transaction system to immediately render payment to the provider using the second tracking number generated in 612. In another embodiment, funding subsystem 214 may employ an ABA number, transit number, routing number, and/or account number for the provider or use an electronic fund transfer service or automatic clearing house to conduct the transaction. In this fashion, a delay that would otherwise occur prior to retailers receiving payment from the TAA is eliminated, and thus, a potential account holder may create, fund, and render payment from a TAA at a point of sale.

Figure 7:
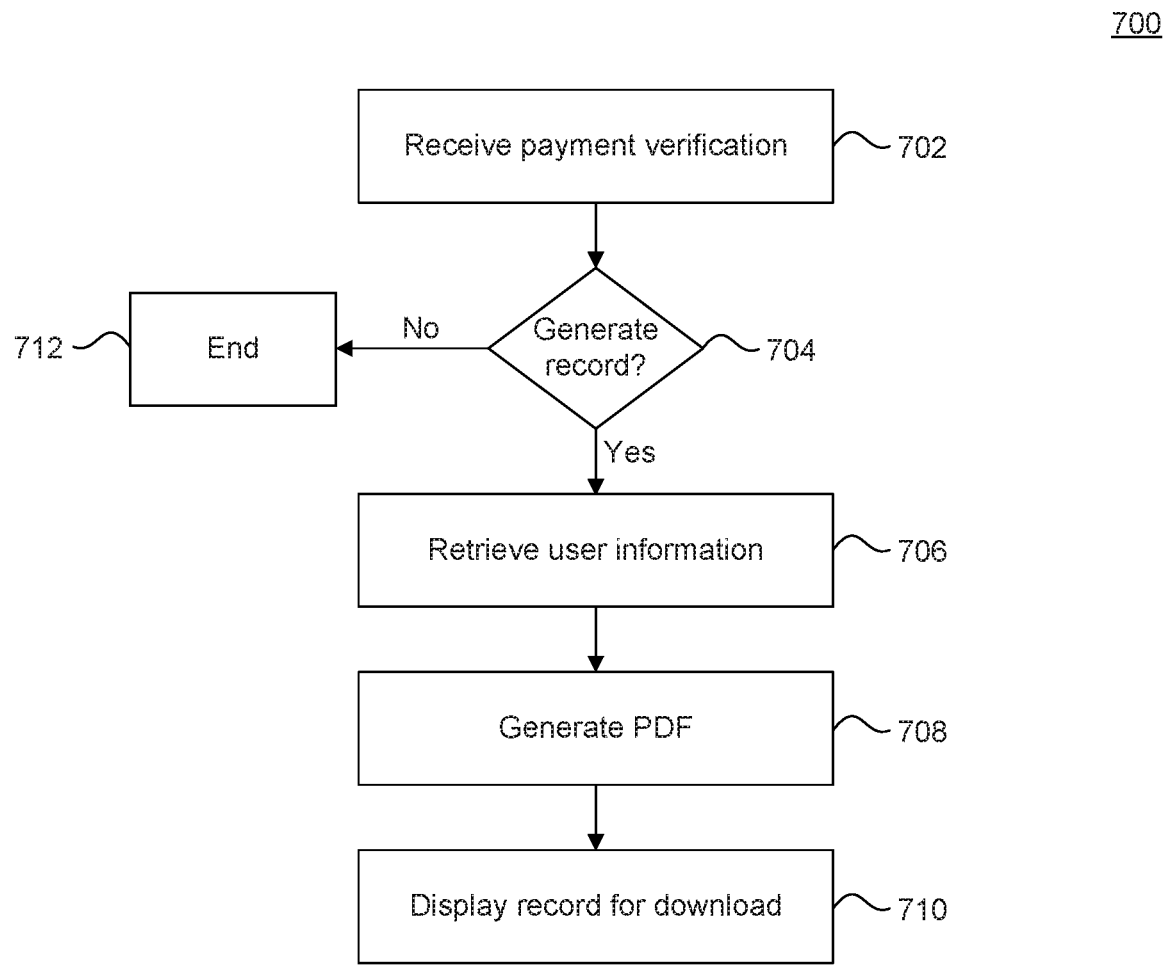
FIG. 7 is a flowchart illustrating steps for generating documentation of a payment of a qualified expense from a newly created TAA, according to an example embodiment.

FIG. 7 illustrates a method 700 for generating documentation of a payment of a qualified expense from a newly created TAA, according to an example embodiment. Method 700 may be performed by processing logic that may include hardware (e.g., circuitry, dedicated logic, programmable logic, microcode, etc.), software (e.g., instructions run on a processing device), or a combination thereof. In an embodiment, some steps in FIG. 7 may not need to be performed in the exact order shown as one skilled in the arts would understand.

In step 702, record generation subsystem 216 receives a payment verification from payment subsystem 414 of provider system 400. The payment verification may include user-identifying information such as full name, social security number, internally generated user identifiers, etc. The verification may further include the service rendered or expenditures accrued, a line-by-line cost for each of the services rendered or expenditures accrued, and relevant bank accounts. The payment verification may further include a record request regarding the qualified expense to be used in step 704.

In step 704, record generation subsystem 216 of management system 200 determines if a user at point-of-sale terminal 110 requested the generation of an appropriately formatted record of the transaction. If not, then method 700 ends. If provider system 400 requested generation of record-keeping, then method 700 proceeds to 706.

In step 706, record generation subsystem 216 may retrieve account holder information needed to generate an appropriate record including the cost of qualified expense, the provider, a doctor name, an address at which the service was provided or received, a description of the service provided, identifying user information, and other suitable information. Record generation subsystem 216 may retrieve information from management database 220 including user tables 221, configuration tables 225, and management transaction log 228. In an alternate embodiment, the requisite information may have been received by record generation subsystem 216 in step 702.

In step 708, record generation subsystem 216 may generate an appropriate record.

Record generation subsystem may create a PDF, DOC, HTML or other suitable file format for downloading. Record generation subsystem 216 may store the generated document in a SAN, NAS, local disk, other suitable locale. Record generation subsystem 216 may add records to management database 220 or management transaction log 228 to catalog the creation of the qualified expense paperwork.

In step 710, record generation subsystem 216 may return the generated document to provider system 400 for downloading and printing. Management UI portal 211 may provide an account holder or representative thereof access to retrieve or download the file via an appropriately formatted web page.

Figure 8:
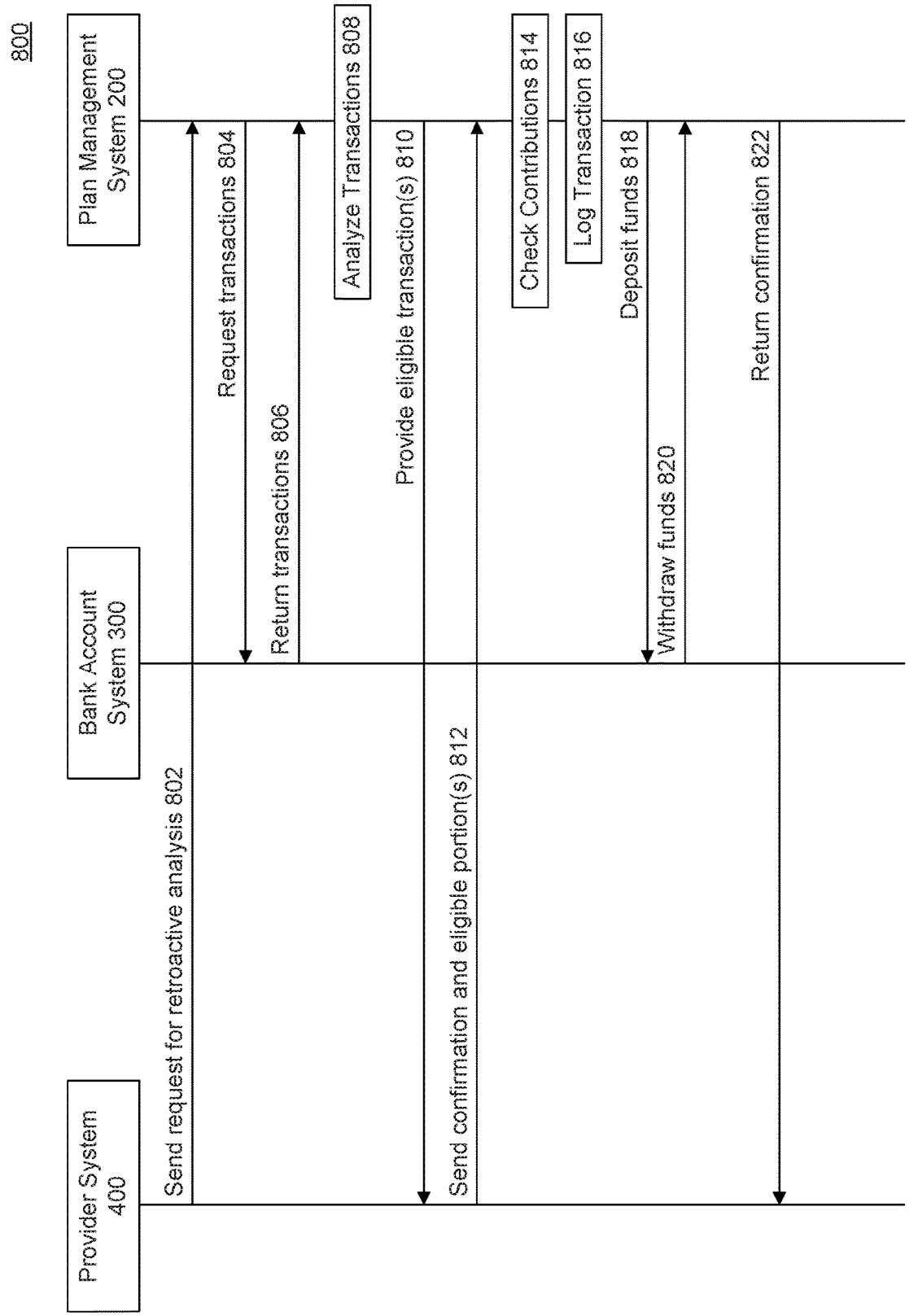
FIG. 8 is a flowchart illustrating steps for performing retroactive analysis of qualified expenses in a plan year, according to an example embodiment.

FIG. 8 illustrates a method 800 for performing retroactive analysis of qualified expenses in a plan year, according to an example embodiment. Retroactive analysis may be performed as part of the Retail HSA process. In other embodiments, retroactive analysis may be applicable when an account holder opens up an account via management UI portal 211, during an asset-transfer-on-demand process, or in response to an account holder's request to perform retroactive analysis at other suitable times. Method 800 may be performed by processing logic that may include hardware (e.g., circuitry, dedicated logic, programmable logic, microcode, etc.), software (e.g., instructions run on a processing device), or a combination thereof. In an embodiment, some steps in FIG. 8 may not need to be performed in the exact order shown, as one skilled in the art would understand.

In 802, provider system 400 may send a request for retroactive analysis to retroactive analysis subsystem 218 in management system 200. The request may be sent because an account holder selects a retroactive-analysis option and provides appropriate parameters during a Retail HSA process. The request may include credentials, e.g. a login/password combination or other authentication information, to one or more bank accounts managed outside of management system 200. While retroactive analysis may initiate at the point of sale as part of the Retail HSA process, in other embodiments, retroactive analysis may occur during the course of other processes, e.g., in response to an account holder's request to perform retroactive analysis for a previously created TAA. In such an embodiment, management system 200, e.g., management UI portal 211, may send the request for retroactive analysis to retroactive analysis subsystem 218.

In 804, retroactive analysis subsystem 218 may request a set of transactions from bank system 300 that occurred during the plan year. In an embodiment, retroactive analysis subsystem 218 may login to each bank account using the credentials provided in 802 and request the transactions conducted in that bank account during the plan year. Retroactive analysis subsystem 218 may formulate appropriate API or function calls to access a service exposed by bank system 300 to complete the request.

In 806, bank system 300 may return the transactions to retroactive analysis subsystem 218. Retroactive analysis subsystem 218 may receive the list of transactions in an appropriate human-readable or machine-interpretable data structure. For example, the list of transactions may be a JSON file with appropriately formatted information about the transactions contained therein, e.g., transaction date, provider name, code, amount, and other suitable details about the transaction. Where the account holder specifies multiple accounts, the process may be iterative, and retroactive analysis subsystem 218 may access multiple bank account system to build an aggregate list of all transactions completed across all of the accounts during a plan year.

In 808, retroactive analysis subsystem 218 may analyze the list of transactions performed during the plan year across the one or more accounts accessed in 804 and 806 to determine transactions corresponding to qualified expenses. Retroactive analysis subsystem 218 may determine the plan year by examining transactions that occurred before the current date but after January $1^{st}$ of the current year. Thus, the plan year will be larger in December $1^{st}$ (consisting of the past 11 months) than in February $1^{st}$ (consisting of only transactions in January). However, in other embodiments and tax systems, a plan year may be determined in other suitable manners. Retroactive analysis subsystem 218 may determine whether an expense is eligible as a qualified expense by comparing the information returned from bank system 300 in 806 to the provider information stored in valid providers 229. For example, valid providers 229 may include a combination of name and code that is relevant to a particular provider, which will match the name-and-code combination returned in the transaction details from the bank. In such an instance, retroactive analysis subsystem 218 may flag the transaction as an eligible transaction. Retroactive analysis subsystem 218 may iteratively, recursively, or sequentially examine each transaction in the aggregate list of transactions returned across all accounts received in 802 and build an aggregate list of eligible transactions by performing the comparison across all items in the list. The aggregate list of eligible transactions may include a provider associated with the transaction, a cost, a date, and other identifying information. Retroactive analysis subsystem 218 may store the aggregate list in a suitable human-readable or machine-interpretable data structure.

In 810, retroactive analysis subsystem 218 may provide the aggregate list of eligible transactions to the account holder either through point-of-sale terminal 110, management UI portal 211, or other suitable means. In an embodiment, retroactive analysis subsystem 218 may present the list chronologically, with the provider name, date, cost, and any information about the transaction included in the presentation. Other suitable presentation methodologies may be employed to similar effect.

In 812, the account holder may provider via provider system 400 or management UI portal 211 with a confirmation and eligible portion for each transaction. The eligible portion may reflect a portion of the total expense that is eligible for a tax deduction. For example, an account holder may view the expenses in rows and enter an eligible portion of the total expense. For some expenses, the eligible portion and the total expense may match, e.g., in a bill paid at a doctor's office. However, for some expenses, the eligible portion may be some amount less than the total expense, e.g., where the account holder made additional purchases simultaneously that are not eligible as qualified expenses. The account holder may also provide a source account or funding source from which to draw the funds in subsequent steps.

In 814, retroactive analysis subsystem 218 may check for over-contributions across the relevant accounts, sum the eligible portions, and enforce other retroactive-analysis rules. To sum the eligible portions, retroactive analysis subsystem 218 may total each eligible portion for each confirmed eligible transaction to determine the aggregate deposit amount. Retroactive analysis subsystem 218 may then enforce rules related to the individual transactions and to the aggregate total. For example, retroactive analysis subsystem 218 may determine if an over-contribution will occur, e.g., if the aggregate amount of transactions exceeds a yearly contribution limit for the TAA. In such an instance, retroactive analysis subsystem 218 may return an alert to the account holder and request further information about the eligible transactions and eligible portions. Retroactive analysis 218 may also analyze the list of transactions and eligible portions to determine an optimized claim structure and remove some eligible portions from the list to get under the yearly contribution limit in optimized fashion. Retroactive analysis subsystem 218 may also analyze the individually specified eligible portions to further assure their tax eligibility.

In 816, record generation subsystem 216 may log the transaction, i.e., create a claim for each eligible transaction confirmed by the account holder across the various subsystems in system 100. For example, transaction manager 215 may create claims within a claims processing subsystem to store appropriate information in management database 220, bank database 320, and/or provider database 420. In one embodiment, funding subsystem 214 may create one claim reflecting the aggregate total determined in 814. However, in another embodiment, record generation subsystem 216 may create a separate claim using funding subsystem 214 for each eligible transaction confirmed by the account holder.

In 818, funding subsystem 214 may deposit funds into the TAA from the funding source specified by the account holder. In one embodiment, funding subsystem 214 may create one transaction that is the aggregate total determined in 814. However, in another embodiment, funding subsystem 214 may create a separate transaction in the banking system by for each eligible transaction confirmed by the account holder. In either event, funding subsystem 214 may transfer the appropriate amount of funds to bank system 300 using a Retail HSA funding and payment mechanism, thereby creating a bank record of the transaction in relevant banking systems that can be associated with the claim generated in 816. In other embodiments, e.g., those outside of the context of the Retail HSA process, funding subsystem 214 may employ an ACH transfer mechanism or other suitable transfer methodology to complete the transferring of funds.

In 820, funding subsystem 214 may withdraw funds from the bank account that funding subsystem 214 deposited in 816. This returns the funds to their original account while creating a record of the transaction in bank system 300 and management system 200 to which generated claims may be associated with.

In 822, management system 200 may return a confirmation to the account holder alerting the account holder that a qualified expenses was created covering the confirmed expenses. In an embodiment, the confirmation may alert the account holder as the transactions that management system 200 finalized. While detailed information may be provided by management system 200 at this stage, a full reporting may not be necessary because the transactions were logged in 816 and thus, may be accounted for in year-end tax reports.

Figure 9:
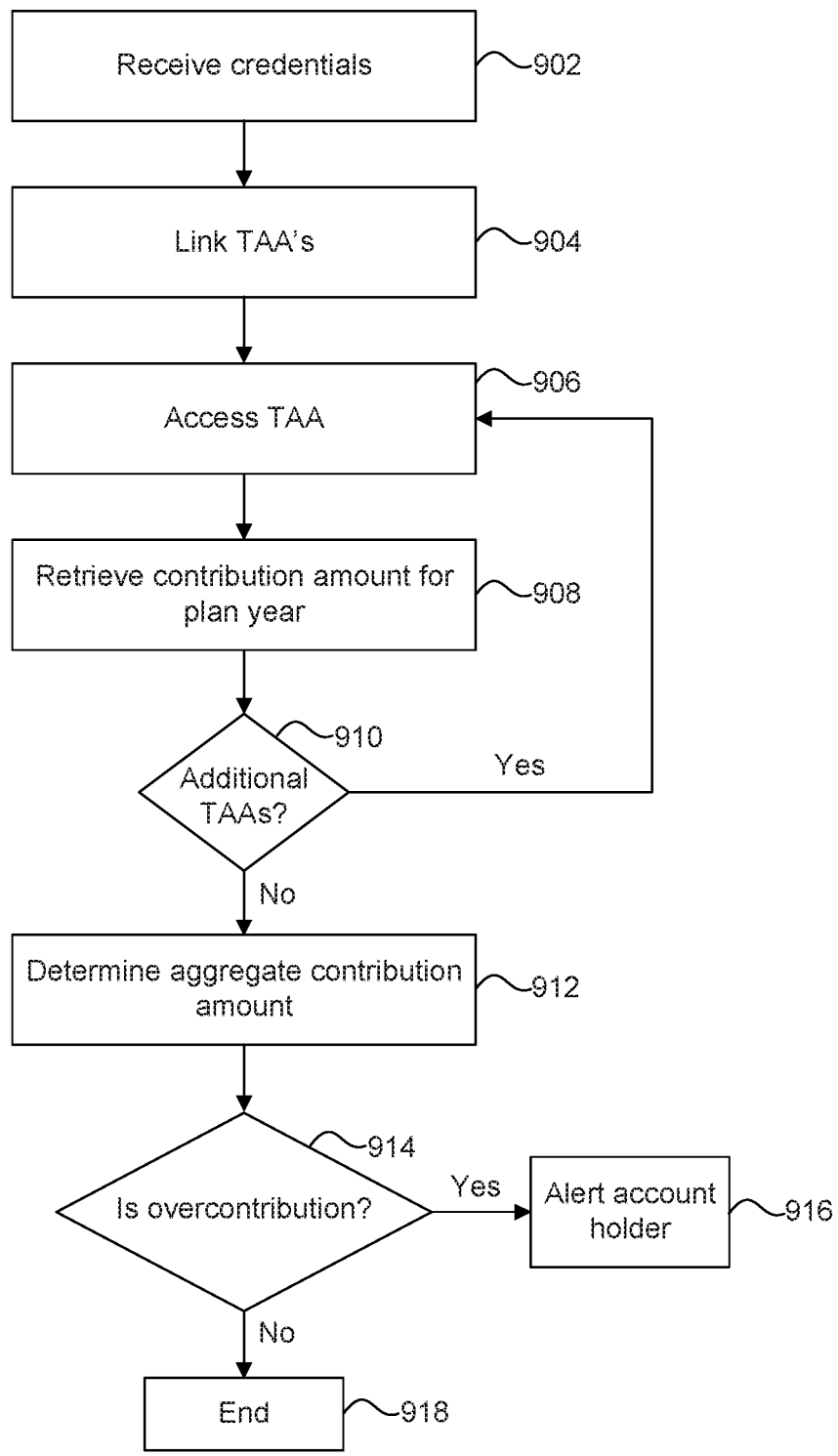
FIG. 9 is a flowchart illustrating steps for performing an over-contribution analysis across linked TAAs, according to an example embodiment.

FIG. 9 illustrates a method 900 for performing an over-contribution analysis across linked TAAs, according to an example embodiment. Method 900 may be performed by processing logic that may include hardware (e.g., circuitry, dedicated logic, programmable logic, microcode, etc.), software (e.g., instructions run on a processing device), or a combination thereof. In an embodiment, some steps in FIG. 9 may not need to be performed in the exact order shown as one skilled in the arts would understand.

In 902, management system 200 may employ over-contribution subsystem 217 to receive credentials from an account holder for externally managed TAAs. Over-contribution subsystem 217 may initiate during the retail HSA process during account creation. In other embodiments, management system 200 may perform over-contribution analysis at other suitable times, for example, in response to an existing account holder requesting that an over-contribution analysis be performed to ensure that tax-eligible transactions were not missed. Account holders may provide credentials that may specify one or more TAAs. These TAAs may be managed in an individual capacity or through another plan manager.

In 904, over-contribution subsystem 217 may store information about the external TAAs specified in 902 in linked accounts 224. Linked accounts 224 may store the account names, encrypted credentials, and other suitable information pertinent to the external TAAs. One skilled in the relevant art(s) will thus appreciate that an over-contribution analysis may occur at a later time of the accounts in linked accounts 224. Thus, in some embodiments, over-contribution subsystem 217 may bypass steps 902 and 904 based on stored information.

In 906, over-contribution subsystem 217 may access a TAA specified in linked accounts 224, as received in 902 or stored previously. Over-contribution subsystem 217 may request the set of transactions from the external system. In an embodiment, over-contribution subsystem 217 may formulate appropriate API or function calls to access a service exposed by the external account servicer. Over-contribution subsystem 217 may receive the TAA information in a suitable format. For example, over-contribution subsystem 217 may receive a JSON file with appropriately formatted information about the TAAs contained therein, e.g., contribution date, amount of contribution, etc.

In 908, over-contribution subsystem 217 may total the contributions that occurred on the external TAA over the course of the plan year. In some embodiments, over-contribution subsystem 217 may receive information from the TAA including the total contribution for a plan year. However, in other embodiments, over-contribution subsystem 217 may receive contributions individually and sum the contributions to determine the contribution amount for the plan year on the TAA.

In 910, over-contribution subsystem 217 of management system 200 determines if additional TAAs received/stored in linked accounts 224 needs to be examined. If yes, then method 900 returns to 906. If no additional TAAs remain to be examined, then method 900 proceeds to 912.

In 912, over-contribution subsystem 217 determines an aggregate contribution amount across the TAA and linked TAAs. In the context of the Retail HSA process, over-contribution subsystem 217 may also additional consider the initial funding amount specified by the prospective account holder. The aggregate contribution amount may thus represent any contribution made by an account holder across all known TAAs as well as any additional contributions currently being processed.

In 914, over-contribution subsystem 217 of management system 200 determines if an over-contribution may occur or may have occurred. Over-contribution subsystem 217 may retrieve a contribution limit suitable to the account type of the relevant TAA. Over-contribution subsystem 217 may then compare the contribution limit to the aggregate contribution amount to see if an over-contribution has occurred or will occur if the current transaction runs to completion. If yes, then method 900 proceeds to 916. If not, then method 900 proceeds to 918, where method 918 ends.

In 916, over-contribution subsystem 217 alerts an account holder as to the potential over-contribution. In the context of the Retail HSA process, over-contribution subsystem 217 may inform the account holder as to the determined aggregate contribution amount for the plan year and list the various amounts and TAAs from which the aggregate contribution amount was determined. Over-contribution subsystem 217 may provide procedural options to remedy the defect, e.g., to render payment from an existing TAA, reduce the initial contribution amount, etc. In other embodiments, over-contribution subsystem 217 may provide appropriate options and remedies to address the over-contributions.

Figure 10:
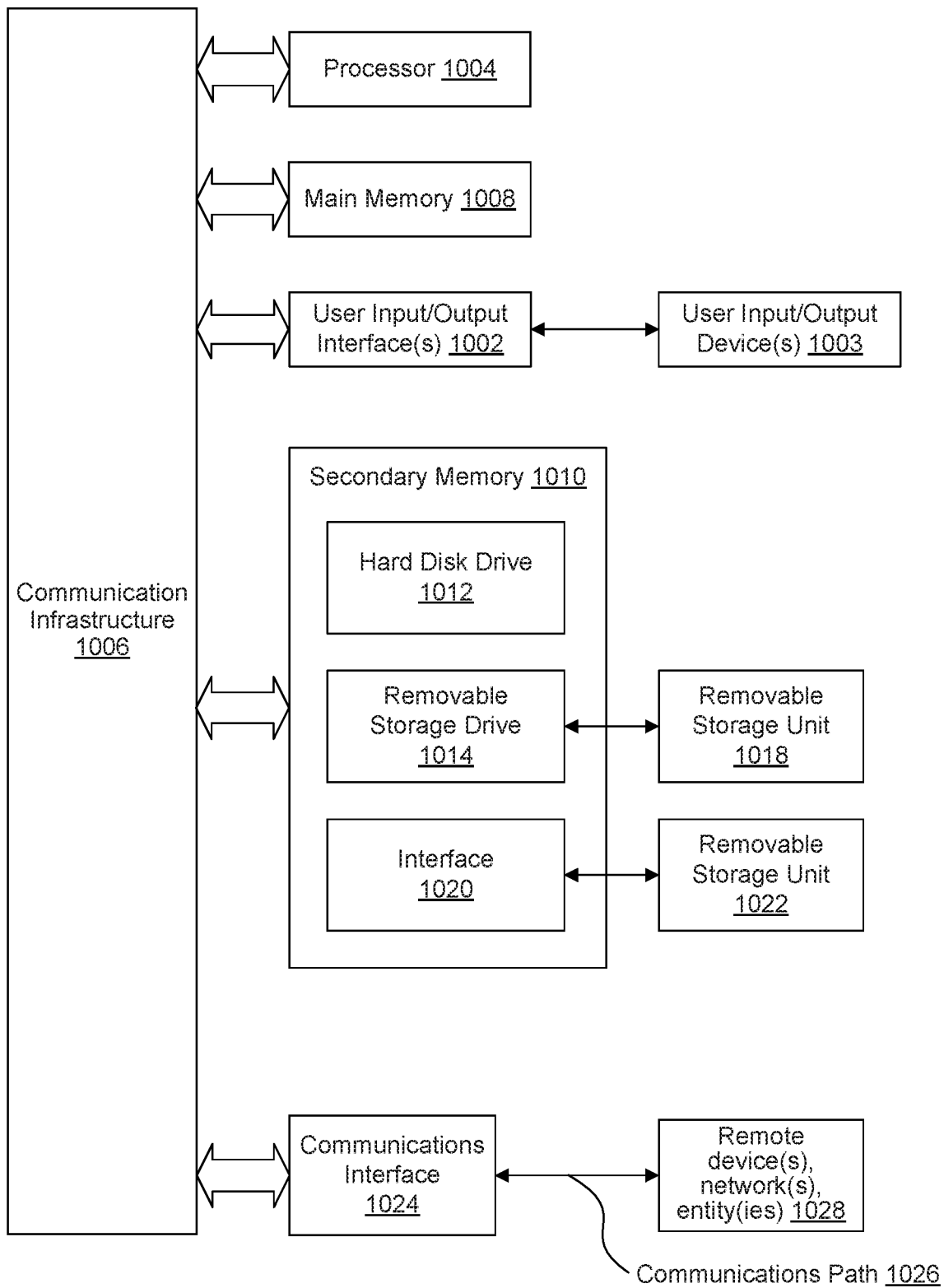
FIG. 10 is an example computer system useful for implementing various embodiments.

Various embodiments may be implemented, for example, using one or more well-known computer systems, such as computer system 1000 shown in FIG. 10. One or more computer systems 1000 may be used, for example, to implement any of the embodiments discussed herein, as well as combinations and sub-combinations thereof.

Computer system 1000 may include one or more processors (also called central processing units, or CPUs), such as a processor 1004. Processor 1004 may be connected to a communication infrastructure or bus 1006.

Computer system 1000 may also include user input/output device(s) 1008, such as monitors, keyboards, pointing devices, etc., which may communicate with communication infrastructure 1006 through user input/output interface(s) 1002.

One or more of processors 1004 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1000 may also include a main or primary memory 1008, such as random access memory (RAM). Main memory 1008 may include one or more levels of cache. Main memory 1008 may have stored therein control logic (i.e., computer software) and/or data.

Computer system 1000 may also include one or more secondary storage devices or memory 1010. Secondary memory 1010 may include, for example, a hard disk drive 1012 and/or a removable storage device or drive 1014. Removable storage drive 1014 may be a floppy disk drive, a magnetic tape drive, a compact disk drive, an optical storage device, tape backup device, and/or any other storage device/drive.

Removable storage drive 1014 may interact with a removable storage unit 1018. Removable storage unit 1018 may include a computer usable or readable storage device having stored thereon computer software (control logic) and/or data. Removable storage unit 1018 may be a floppy disk, magnetic tape, compact disk, DVD, optical storage disk, and/any other computer data storage device. Removable storage drive 1014 may read from and/or write to removable storage unit 1018.

Secondary memory 1010 may include other means, devices, components, instrumentalities or other approaches for allowing computer programs and/or other instructions and/or data to be accessed by computer system 1000. Such means, devices, components, instrumentalities or other approaches may include, for example, a removable storage unit 1022 and an interface 1020. Examples of the removable storage unit 1022 and the interface 1020 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1000 may further include a communication or network interface 1024. Communication interface 1024 may enable computer system 1000 to communicate and interact with any combination of external devices, external networks, external entities, etc. (individually and collectively referenced by reference number 1028). For example, communication interface 1024 may allow computer system 1000 to communicate with external or remote devices 1028 over communications path 1026, which may be wired and/or wireless (or a combination thereof), and which may include any combination of LANs, WANs, the Internet, etc. Control logic and/or data may be transmitted to and from computer system 1000 via communication path 1026.

Computer system 1000 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 1000 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 1000 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1000, main memory 1008, secondary memory 1010, and removable storage units 1018 and 1022, as well as tangible articles of manufacture embodying any combination of the foregoing. Such control logic, when executed by one or more data processing devices (such as computer system 1000), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 10. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A method, comprising:
receiving, by one or more processors, a creation request at a point of sale to create a tax-advantaged account (TAA), wherein the creation request comprises an account holder, an expenditure amount, a provider, an initial funding amount, and a funding account;
creating, by the one or more processors, the TAA comprising a TAA balance and a card number, wherein the TAA is associated with the account holder and linked to the funding account;
creating, by the one or more processors, a first tracking value representing a first authorization of payment from the funding account to the TAA balance and a second tracking value representing a second authorization of payment from the TAA balance to the provider account;
locking, by the one or more processors, a record of the initial contribution amount at the funding account until completion of a transfer of the expenditure amount to the provider via a peer-to-peer-funding mechanism;
transferring, by the one or more processors, the initial funding amount from the funding account to the TAA balance via the peer-to-peer funding mechanism using the first tracking value; and
transferring in real-time, by the one or more processors, the expenditure amount from the TAA balance to a provider account associated with the provider via the peer-to-peer funding mechanism using the card number and the second tracking value.

2. The method of claim 1, further comprising:
sending, by the one or more processors, a provider confirmation to the provider that includes the second tracking value and the card number.

3. The method of claim 1, further comprising:
receiving, by the one or more processors, login credentials for a second TAA;
linking, by the one or more processors, the second TAA and the TAA;
accessing, by the one or more processors, the second TAA to determine a total contribution amount for the second TAA for a plan year;
adding, by the one or more processors, the total contribution amount to the initial funding amount to determine an aggregate contribution amount for the plan year;
comparing, by the one or more processors, the aggregate contribution amount to a funding limit for the plan year to determine an over-contribution; and
providing, by the one or more processors, an alert to the account holder about the over-contribution prior to creating and funding the TAA.

4. The method of claim 1, further comprising:
providing, by the one or more processors, a crediting option to the account holder when receiving the creation request, wherein the crediting option comprises a credit amount, a credit source, and credit terms;
receiving, by the one or more processors, an acceptance of the credit terms from the account holder; and
transferring, by the one or more processors, the credit amount from the credit source to the TAA balance using the peer-to-peer funding mechanism.

5. The method of claim 1, further comprising:
receiving, by the one or more processors, login credentials to an external account;
accessing, by the one or more processors, one or more transactions that occurred in the external account during a plan year;
determining, by the one or more processors, an eligible transaction comprising a transaction amount and a transaction date from the one or more transactions by comparing a provider associated with the eligible transaction to a list of valid providers stored in a management database of the account manager;
providing, by the one or more processors, the transaction amount and the transaction date to the account holder;
receiving, by the one or more processors, a confirmation and an eligible portion related to the eligible transaction;
depositing, by the one or more processors, the eligible portion into the TAA balance using the peer-to-peer funding mechanism; and
withdrawing, by the one or more processors, the eligible portion from the TAA balance using the peer-to-peer funding mechanism to create a tax-advantaged transaction for the account holder.

6. The method of claim 5, further comprising:
determining, by the one or more processors, a second eligible transaction comprising a second transaction amount and a second transaction date from the one or more transactions by comparing a transaction associated with the second eligible transaction to a database of valid providers stored in the management database;
providing, by the one or more processors, the second transaction amount and the second transaction date to the account holder;
receiving, by the one or more processors, a second confirmation and a second eligible portion related to the second eligible transaction;
adding, by the one or more processors, the second eligible portion to the eligible portion to determine an aggregated eligible portion;
depositing, by the one or more processors, the aggregated eligible portion into the TAA balance using the peer-to-peer funding mechanism; and
withdrawing, by the one or more processors, the aggregated eligible portion from the TAA balance using the peer-to-peer funding mechanism to create an aggregated tax-advantaged transaction for the account holder.

7. The method of claim 5, wherein the list of valid providers comprises a provider name, a provider code, a location identifier, and an insurance code.

8. A system, comprising:
a processor; and
a memory having instructions stored thereon that, when executed by the processor, cause the processor to:
receive a creation request at a point of sale to create a tax-advantaged account (TAA), wherein the creation request comprises an account holder, an expenditure amount, a provider, an initial funding amount, and a funding account;
create the TAA comprising a TAA balance and a card number, wherein the TAA is associated with the account holder and linked to the funding account;
create a first tracking value representing a first authorization of payment from the funding account to the TAA balance and a second tracking value representing a second authorization of payment from the TAA balance to the provider account lock a record of the initial contribution amount at the funding account until completion of a transfer of the expenditure amount to the provider via a peer-to-peer-funding mechanism;
transfer the initial funding amount from the funding account to the TAA balance via the peer-to-peer funding mechanism using the first tracking value; and
transfer in real-time the expenditure amount from the TAA balance to a provider account associated with the provider via the peer-to-peer funding mechanism using the card number and the second tracking value.

9. The system of claim 8, the processor further configured to:
send a provider confirmation to the provider that includes the second tracking value and the card number.

10. The system of claim 8, the processor further configured to:
receive login credentials for a second TAA;
link the second TAA and the TAA;
access the second TAA to determine a total contribution amount for the second TAA for a plan year;
add the total contribution amount to the initial funding amount to determine an aggregate contribution amount for the plan year;
compare the aggregate contribution amount to a funding limit for the plan year to determine an over-contribution; and
provide an alert to the account holder about the over-contribution prior to creating and funding the TAA.

11. The system of claim 8, the processor further configured to:
provide a crediting option to the account holder when receiving the creation request, wherein the crediting option comprises a credit amount, a credit source, and credit terms;
receive an acceptance of the credit terms from the account holder; and
transfer the credit amount from the credit source to the TAA balance using the peer-to-peer funding mechanism.

12. The system of claim 8, the processor further configured to:
receive login credentials to an external account;
access one or more transactions that occurred in the external account during a plan year;
determine an eligible transaction comprising a transaction amount and a transaction date from the one or more transactions by comparing a provider associated with the eligible transaction to a list of valid providers stored in a management database of the account manager;
provide the transaction amount and the transaction date to the account holder;
receive a confirmation and an eligible portion related to the eligible transaction;
deposit the eligible portion into the TAA balance using the peer-to-peer funding mechanism; and
withdraw the eligible portion from the TAA balance using the peer-to-peer funding mechanism to create a tax-advantaged transaction for the account holder.

13. The system of claim 12, the processor further configured to:
determine a second eligible transaction comprising a second transaction amount and a second transaction date from the one or more transactions by comparing a transaction associated with the second eligible transaction to a database of valid providers stored in the management database;
provide the second transaction amount and the second transaction date to the account holder;
receive a second confirmation and a second eligible portion related to the second eligible transaction;
add the second eligible portion to the eligible portion to determine an aggregated eligible portion;
deposit the aggregated eligible portion into the TAA balance using the peer-to-peer funding mechanism; and
withdraw the aggregated eligible portion from the TAA balance using the peer-to-peer funding mechanism to create an aggregated tax-advantaged transaction for the account holder.

14. The system of claim 12, wherein the list of valid providers comprises a provider name, a provider code, a location identifier, and an insurance code.

15. A non-transitory computer-readable device having instructions stored thereon that, when executed by at least one computing device, cause the at least one computing device to perform operations comprising:
receiving a creation request at a point of sale to create a tax-advantaged account (TAA), wherein the creation request comprises an account holder, an expenditure amount, a provider, an initial funding amount, and a funding account;

creating the TAA comprising a TAA balance and a card number, wherein the TAA is associated with the account holder and linked to the funding account;

creating a first tracking value representing a first authorization of payment from the funding account to the TAA balance and a second tracking value representing a second authorization of payment from the TAA balance to the provider account locking a record of the initial contribution amount at the funding account until completion of a transfer of the expenditure amount to the provider via a peer-to-peer-funding mechanism;

transferring the initial funding amount from the funding account to the TAA balance via the peer-to-peer funding mechanism using the first tracking value; and transferring in real-time the expenditure amount from the TAA balance to a provider account associated with the provider via the peer-to-peer funding mechanism using the card number and the second tracking value.

16. The non-transitory computer-readable device of claim 15, the operations further comprising:

sending a provider confirmation to the provider that includes the second tracking value and the card number.

17. The non-transitory computer-readable device of claim 15, the operations further comprising:

receiving login credentials for a second TAA;

linking the second TAA and the TAA;

accessing the second TAA to determine a total contribution amount for the second TAA for a plan year;

adding the total contribution amount to the initial funding amount to determine an aggregate contribution amount for the plan year;

comparing the aggregate contribution amount to a funding limit for the plan year to determine an over-contribution; and providing an alert to the account holder about the over-contribution prior to creating and funding the TAA.

18. The non-transitory computer-readable device of claim 15, the operations further comprising:

providing a crediting option to the account holder when receiving the creation request, wherein the crediting option comprises a credit amount, a credit source, and credit terms;

receiving an acceptance of the credit terms from the account holder; and transferring the credit amount from the credit source to the TAA balance using the peer-to-peer funding mechanism.

19. The non-transitory computer-readable device of claim 15, the operations further comprising:

receiving login credentials to an external account;

accessing one or more transactions that occurred in the external account during a plan year;

determining an eligible transaction comprising a transaction amount and a transaction date from the one or more transactions by comparing a provider associated with the eligible transaction to a list of valid providers stored in a management database of the account manager;

providing the transaction amount and the transaction date to the account holder;

receiving a confirmation and an eligible portion related to the eligible transaction;

depositing the eligible portion into the TAA balance using the peer-to-peer funding mechanism; and withdrawing the eligible portion from the TAA balance using the peer-to-peer funding mechanism to create a tax-advantaged transaction for the account holder.

20. The non-transitory computer-readable device of claim 19, the operations further comprising:

determining a second eligible transaction comprising a second transaction amount and a second transaction date from the one or more transactions by comparing a transaction associated with the second eligible transaction to a database of valid providers stored in the management database;

providing the second transaction amount and the second transaction date to the account holder;

receiving a second confirmation and a second eligible portion related to the second eligible transaction;

adding the second eligible portion to the eligible portion to determine an aggregated eligible portion;

depositing the aggregated eligible portion into the TAA balance using the peer-to-peer funding mechanism; and withdrawing the aggregated eligible portion from the TAA balance using the peer-to-peer funding mechanism to create an aggregated tax-advantaged transaction for the account holder.

* * * * *